(12) United States Patent
Liljegren et al.

(10) Patent No.: US 6,998,517 B1
(45) Date of Patent: Feb. 14, 2006

(54) **CONTROL OF FRUIT DEHISCENCE IN *ARABIDOPSIS* BY INDEHISCENT1 GENES**

(75) Inventors: Sarah Liljegren, La Jolla, CA (US); Martin F. Yanofsky, San Diego, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 09/548,971

(22) Filed: Apr. 13, 2000

Related U.S. Application Data

(63) Continuation-in-part of application No. 09/339,998, filed on Jun. 25, 1999, now Pat. No. 6,410,826.

(60) Provisional application No. 60/090,649, filed on Jun. 25, 1998.

(51) Int. Cl.
  A01H 1/00     (2006.01)
  A01H 5/00     (2006.01)
  C12N 15/82    (2006.01)

(52) U.S. Cl. .................. 800/290; 435/320.1; 800/294; 800/298; 800/306

(58) Field of Classification Search ............... 536/23.7; 435/320.1, 468, 469; 800/290, 294, 287, 800/286, 298
See application file for complete search history.

(56) References Cited

FOREIGN PATENT DOCUMENTS

| WO | WO 94/23043   | 10/1994 |
| WO | WO 96 30529 A | 10/1996 |
| WO | WO 97/13865   | 4/1997  |
| WO | WO 97 13865 A | 4/1997  |
| WO | WO 98/22592   | 5/1998  |
| WO | WO 99 00502 A | 1/1999  |
| WO | WO 99 49046 A | 9/1999  |

OTHER PUBLICATIONS

Ryan et al. Genebank Accession No. AF069299, submitted Jun. 9, 1998, Gene "F6N15.18".*
Ellis et al 1987, The EMBO Journal 6(1):11-16.*
Quattrocchio et al 1998, The Plant Journal 13(4):475-488.*
Colliver et al 1997, Plant Molecular Biology 35:509-522.*
Riechmann et al 2000, Science 290:2105-2110.*
A. Ros Barceló, "Lignification in Plant Cell Walls"; *International Review of Cytology*, vol. 176, p. 87-132 (1997).
Coupe et al., "Identification and characterization of a proline-rich mRNA that accumulates during pod development in oilseed rape (*Brassica napus* L.),"; *Plant Mol. Biol.* 23:1223-1232 (1993).
Dixon, et al., "Metabolic engineering: prospects for crop improvement through the genetic manipulation of phenylpropanoid biosynthesis and defense responses—a review," *Gene* 179:61-71 (1996).
Erskine, "Selection for Pod Retention and Pod Indehiscence in Lentils," *Euphytica* 34:105-112 (1985).
Flanagan et al, "Specific expression of the *AGL1* MADS-box gene suggests regulatory functions in *Arabidopsis* gynoecium and ovule development," *The Plant Journal* 10:343-353 (1996).
Gillaspy et al., "Fruits: A Developmental Perspective," *The Plant Cell* 5:1439-1451 (1993).
Gu, et al., "The FRUITFULL MADS-box gene mediates cell differentiation during Arabidopsis fruit development"; *Development* 125:1509-1517 (1998).
Hempel et al., "Floral determination and expression of floral regulatory genes in *Arabidopsis,*" *Development* 124:3845-3853 (1997).
Kempin et al., "Targeted disruption in *Arabidopsis,*" *Nature* 389:802-803 (1997).
Ma, et al., "*AGL1-AGL6*, an *Arabidopsis* gene family with similarity to floral homeotic and transcription factor genes," *Genes & Development* 5:484-495 (1991).
Mandel and Yanofsky, "The Arabidopsis *AGL8* MADS Box Gene Is Expressed in Inflorescence Meristems and Is Negatively Regulated by *APETALA1*" *The Plant Cell* 7: 1763-1771 (Nov. 1995).
Meakin and Roberts, "Dehiscence of Fruit in Oilseed Rape (*Brassica napus* L.): The Role of Cell Wall Degrading Enzymes and Ethylene," *Journal of Experimental Botany* 41:1003-1011 (Aug. 1990).
Meakin and Roberts, "Dehiscence of Fruit in Oilseed Rape (*Brassica napus* L): Anatomy of Pod Dehiscence," *Journal of Experimental Botany* 41:995-1002 (Aug. 1990).
Mena, et al., "A characterization of the MADS-box gene family in maize"; *The Plant Journal,* 8(6) 845-854 (1995).
Menzel, et al., "Identification of two MADS box genes that are expressed in the apical meristem of the long-day plant *Sinapis alba* in transition to flowering," *The Plant Journal* 9:399-408 (1996).
Mizukami, et al, "Functional domains of the floral regulator AGAMOUS: characterization of the DNA binding domain and analysis of dominant negative mutations," *Plant Cell* 8:831-845 (May 1996).
Petersen, et al., "Isolation and characterization of a pod dehiscence zone-specific polygalacturonase from *Brassica napus,*" *Plant Mol. Biol.* 31:517-527 (1996).
Purugganan, "The MADS-Box Floral Homeotic Gene Lineages Predate the Origin of Seed Plants: Phylogenetic and Molecular Clock Estimates"; *J. Mol. Evol.* 45:392-396 (1997).
Purugganan, et al., "Molecular Evolution of Flower Development: Diversification of the Plant MADS-box Regulatory Gene Family," *Genetics* 140:345-356 (May 1995).

(Continued)

*Primary Examiner*—David H Kruse
(74) *Attorney, Agent, or Firm*—Townsend and Townsend and Crew LLP

(57) ABSTRACT

The present invention provides methods and compositions that modulate fruit dehiscence in plants.

45 Claims, 1 Drawing Sheet

OTHER PUBLICATIONS

Riechmann and Meyerowitz, "MADS Domain Proteins in Plant Development," *Biol. Chem.* 378:1079-1101 (Oct. 1997).

Savidge, et al., "Temporal Relationship between the Transcription of Two Arabidopsis MADS Box Genes and the Floral Organ Identity Genes," *The Plant Cell* 7:721-733 (Jun. 1995).

Sundaresan, et al., "Patterns for gene action in plant development revealed by enhancer trap and gene trap transposable elements," *Genes Devel.* 9:1797-1810 (1995).

Whetten and Sederoff, "Genetic engineering of wood"; *Forest Ecology and Management* 43:301-316 (1991).

Yanofsky, "Floral Meristems to Floral Organs: Genes Controlling Early Events in *Arabidopsis* Flower Development," *Annual Rev. Plant Physiol. Plant Mol. Biol.* 46:167-188 (1995).

Yanofsky, et al., "The Protein encoded by the *Arabidopsis* homeotic gene *agamous* resembles transcription factors," *Nature* 346:35-39 (Jul. 1990).

Genbank Accession No. AAC19297 submitted May 29, 1998.

Genbank Accession No. AF038863 submitted Dec. 14, 1997.

Genbank Accession No. AF038864 submitted Dec. 14, 1997.

Genbank Accession No. AF069299 submitted May 29, 1998.

Genbank Accession No. AI486645 submitted Mar. 8, 1999.

Database EMBL Sequence Library 'Online! Mar. 16, 2000 EU Arabidopsis Sequence Project: "*Arabidopsis thaliana* DNA chromosome 4, contig fragment No. 1" accession No. AI161471.

Database TREMBL Database 'Online! Nov. 1, 1998 Ryan, E., Edwards, J., Pape, K., "The sequence of A. thaliana F6N15" accession No. 081313.

Database EMBL Sequence Library 'Online! Oct. 13, 1997 Rounsley S.D., Kelley J.M., Field C.E., Craven M.B., Adams M.D., Venter J.C.: "Use of a BAC End sequence Database To Identify Minimal Overlaps for Arabidopsis Genomic Sequence—F2G15TF IGF *Arabidopsis thaliana* genomic clone F2G15, genomic survey sequence" accession No. B26402.

Database EMBL Sequence Library 'Online! Jan. 31, 2000 Buell C.R., et al.: "Genomic survey sequencing of Landsberg erecta ecotype of *Arabidopsis thaliana* and identification of sequence-based polymorphisms—LERAM13TR LERA *Arabidopsis thaliana* genomic clone LERAM13, genomic survey sequence" accession No. AQ956795.

Sundaresan V et al: "Patterns of Gene Action in Plant Development Revealed by Enhancer Trap and Gene Trap Transposable Elements" Genes and Development, Cold Spring Harbor, NY, US, vol. 9, No. 14, Jul. 15, 1995, pp. 1797-1810.

* cited by examiner

CONTROL OF FRUIT DEHISCENCE IN *ARABIDOPSIS* BY INDEHISCENT1 GENES

CROSS-REFERENCES TO RELATED APPLICATIONS

This application is a continuation-in-part of U.S. application Ser. No. 09/339,998, filed on Jun. 25, 1999, now U.S. Pat. No. 6,410,826, issued on Jun. 25, 2002, which claims benefit of priority to U.S. Provisional Application No. 60/090,649, filed Jun. 25, 1998, each of which is incorporated by reference in its entirety.

STATEMENT AS TO RIGHTS TO INVENTIONS MADE UNDER FEDERALLY SPONSORED RESEARCH AND DEVELOPMENT

This invention was made with Government support under National Science Foundation Grant number IBN-9985530. The Government has certain rights in the invention.

FIELD OF THE INVENTION

This invention relates plant genetic engineering. In particular, the invention relates to methods and compositions that modulate fruit dehiscence in plants.

BACKGROUND OF THE INVENTION

Rapeseed is one of the most important oilseed crops after soybeans and cottonseed, representing 10% of the world oilseed production in 1990. Rapeseed contains 40% oil, which is pressed from the seed, leaving a high-protein seed meal of value for animal feed and nitrogen fertilizer. Rapeseed oil, also known as canola oil, is a valuable product, representing the fourth most commonly traded vegetable oil in the world.

Unfortunately, the yield of seed from rapeseed and related plants is limited by pod dehiscence, which is a process that occurs late in fruit development whereby the pod is opened and the enclosed seeds released. Degradation and separation of cell walls along a discrete layer of cells dividing the two halves of the pod, termed the "dehiscence zone," result in separation of the two halves of the pod and release of the contained seeds. The dehiscence zone is a region of only one to three cells in width that extends along the entire length of the valve/replum boundary (Meakin and Roberts, *J. Exp. Botany* 41:995–1002 (1990)). As the cells in the dehiscence zone separate from one another, the valves detach from the replum, allowing seeds to be dispersed. Seed "shattering," whereby seeds are prematurely shed through dehiscence before the crop can be harvested, is a significant problem faced by commercial seed producers and represents a loss of income to the industry. Adverse weather conditions can exacerbate the process of dehiscence, resulting in greater than 50% loss of seed yield.

The fruit, a complex structure unique to flowering plants, mediates the maturation and dispersal of seeds. In most flowering plants, the fruit consists of the pericarp, which is derived from the ovary wall, and the seeds, which develop from fertilized ovules. *Arabidopsis*, which is typical of the more than 3000 species of the *Brassicaceae*, produces fruit in which the two carpel valves (ovary walls) are joined to the replum, a visible suture that divides the two carpels.

The plant hormone ethylene is produced by developing seeds and appears to be an important regulator of the dehiscence process. One line of evidence supporting a role for ethylene in regulation of dehiscence comes from studies of fruit ripening, which, like fruit dehiscence, is a process involving the breakdown of cell wall material. In fruit ripening, ethylene acts in part by activating cell wall degrading enzymes such as polygalacturonase (Theologis et al., *Develop. Genetics* 14:282–295 (1993)). Moreover, in genetically modified tomato plants in which the ethylene response is blocked, such as transgenic tomato plants expressing antisense polygalacturonase, there is a significant delay in fruit ripening (Lanahan et al., *The Plant Cell* 6:521–530 (1994); Smith et al., *Nature* 334:724–726 (1988)).

In dehiscence, ultrastructural changes that culminate in degradation of the middle lamella of dehiscence zone cell walls weaken rapeseed pods and eventually lead to pod shatter. As in fruit ripening, hydrolytic enzymes including polygalacturonases play a role in this programmed breakdown. For example, in oilseed rape, a specific endo-polygalacturonase, RDPG1, is upregulated and expressed exclusively in the dehiscence zone late in pod development (Petersen et al., *Plant Mol. Biol.* 31:517–527 (1996), which is incorporated herein by reference). Ethylene may regulate the activity of hydrolytic enzymes involved in the process of dehiscence as it does in fruit ripening (Meakin and Roberts, *J. Exp. Botany* 41:1003–1011 (1990), which is incorporated herein by reference). Yet, until now, the proteins that control the process of dehiscence, such as those regulating the relevant hydrolytic enzymes, have eluded identification.

Attempts to solve the problem of pod shatter and early fruit dehiscence over the past 20 years have focused on the breeding of shatter-resistant varieties. However, these plant hybrids are frequently sterile and lose favorable characteristics that must be regained by backcrossing, which is both time-consuming and laborious. Other strategies to alleviate pod shattering include the use of chemicals such as pod sealants or mechanical techniques such as swathing to reduce wind-stimulated shattering. To date, however, a simple method for producing genetically modified plants that do not open and release their seeds prematurely has not been described.

Thus, a need exists for identifying genes that regulate the dehiscence process and for developing genetically modified plant varieties in which the natural seed dispersal process is delayed. The present invention satisfies this need and provides related advantages as well.

SUMMARY OF THE INVENTION

This invention provides an isolated nucleic acid comprising an IND1 polynucleotide sequence encoding an IND1 polypeptide at least 70% identical to SEQ ID NO:2. The isolated nucleic acid, for instance, can comprise a polynucleotide that encodes SEQ ID NO:2. In another embodiment, the isolated nucleic acid, for instance, can comprise positions from about 2765 to about 3361 of SEQ ID NO:1. For example, the nucleic acid can comprise SEQ ID NO:1.

The present invention also provides an expression cassette comprising a promoter operably linked to an IND1 polynucleotide sequence, or complement thereof, encoding an IND1 polypeptide at least about 70% identical to SEQ ID NO:1. The expression cassette, for instance, can comprise a polynucleotide that encodes SEQ ID NO:2. In another embodiment, the expression cassette, for instance, can comprise positions from about 2765 to about 3361 of SEQ ID NO:1. For example, the expression cassette can comprise SEQ ID NO:1. In some embodiments, the expression cassette comprises a promoter. The promoter, for instance, can be constitutive or tissue specific. In one aspect of the invention, the promoter is a dehiscence zone specific promoter. In another aspect, the promoter can comprise positions from about 1 to about 2764 or positions from about 3362 to about 3856 of SEQ ID NO:1.

The present invention also provides a plant comprising a recombinant expression cassette comprising a promoter operably linked to a polynucleotide sequence encoding an IND1 polypeptide at least about 70% identical to SEQ ID NO:1. In one aspect, the polynucleotide sequence encoding the IND1 polypeptide is operably linked to the promoter in the antisense orientation. In another aspect, the polynucleotide sequence encoding the IND1 polypeptide is operably linked to the promoter in the sense orientation. The polynucleotide sequence can further comprise a second polynucleotide sequence encoding the IND1 polypeptide wherein the second polynucleotide sequence is operably linked to a second promoter in the antisense orientation. In some embodiments, the plant of the invention has reduced lignification in valve margin cells. In other embodiments, the promoter is a dehiscence zone-selective regulatory element. In some of these embodiments, the regulatory element comprises positions from about 1 to about 2764 or from about 3362 to about 3856 of SEQ ID NO:1.

The present invention also provides a method of delaying fruit dehiscence in a plant comprising suppressing expression of an IND1 nucleic acid in the plant by introducing into the plant a recombinant expression cassette comprising a promoter operably linked to a polynucleotide sequence encoding an IND1 polypeptide at least 70% identical to SEQ ID NO:2. In some embodiments, the IND1 polypeptide is SEQ ID NO:2. In other embodiments, the IND1 polynucleotide comprises positions from about 2765 to about 3361 of SEQ ID NO:1. In one aspect of the invention, the IND1 polynucleotide comprises SEQ ID NO:1. The method can include a polynucleotide sequence encoding the IND1 polypeptide operably linked to the promoter in the antisense orientation. In another embodiment, the promoter is linked to the promoter is the sense orientation. The polynucleotide sequence can further comprise a second polynucleotide sequence encoding the IND1 polypeptide wherein the second polynucleotide sequence is operably linked to a second promoter in the antisense orientation. In some embodiments, the method results in a plant with reduced lignification in valve margin cells. In other embodiments, the promoter is a dehiscence zone-selective regulatory element. In some of these embodiments, the regulatory element comprises positions from about 1 to about 2764 or from about 3362 to about 3856 of SEQ ID NO:1. In one aspect, the recombinant expression cassette is introduced into the plant with *Agrobacterium*.

The present invention also provides a method of delaying fruit dehiscence in a plant comprising suppressing expression of an IND1 gene in the plant by introducing into the plant a recombinant expression cassette comprising a polynucleotide sequence at least about 70% identical to positions from about 1 to about 2764 or from about 3362 to about 3856 of SEQ ID NO:1. In one aspect of the invention, the polynucleotide sequence comprises positions from about 1 to about 2764 or from about 3362 to about 3856 of SEQ ID NO:1. In some aspects, lignification is reduced in valve margin cells.

Definitions

The phrase "nucleic acid" refers to a single or double-stranded polymer of deoxyribonucleotide or ribonucleotide bases read from the 5' to the 3' end. Nucleic acids may also include modified nucleotides that permit correct read through by a polymerase and do not alter expression of a polypeptide encoded by that nucleic acid.

The phrase "polynucleotide sequence" or "nucleic acid sequence" includes both the sense and antisense strands of a nucleic acid as either individual single strands or in the duplex. It includes, but is not limited to, self-replicating plasmids, chromosomal sequences, and infectious polymers of DNA or RNA.

The phrase "nucleic acid sequence encoding" refers to a nucleic acid which directs the expression of a specific protein or peptide. The nucleic acid sequences include both the DNA strand sequence that is transcribed into RNA and the RNA sequence that is translated into protein. The nucleic acid sequences include both the full length nucleic acid sequences as well as non-full length sequences derived from the full length sequences. It should be further understood that the sequence includes the degenerate codons of the native sequence or sequences which may be introduced to provide codon preference in a specific host cell.

The term "promoter" or "regulatory element" refers to a region or sequence determinants located upstream or downstream from the start of transcription and which are involved in recognition and binding of RNA polymerase and other proteins to initiate transcription. A "plant promoter" is a promoter capable of initiating transcription in plant cells. Such promoters need not be of plant origin, for example, promoters derived from plant viruses, such as the CaMV35S promoter, can be used in the present invention.

As used herein, the term "dehiscence zone-selective regulatory element" refers to a nucleotide sequence that, when operatively linked to a nucleic acid molecule, confers selective expression upon the operatively linked nucleic acid molecule in a limited number of plant tissues, including the valve margin or dehiscence zone. The valve margin is the future site of the dehiscence zone and encompasses the margins of the outer replum as well as valve cells adjacent to the outer replum. The dehiscence zone, which develops in the region of the valve margin, refers to the group of cells that separate during the process of dehiscence, allowing valves to come apart from the replum and the enclosed seeds to be released. Thus, a dehiscence zone-selective regulatory element, as defined herein, confers selective expression in the mature dehiscence zone, or confers selective expression in the valve margin, which marks the future site of the dehiscence zone.

A dehiscence zone-selective regulatory element can confer specific expression exclusively in cells of the valve margin or dehiscence zone or can confer selective expression in a limited number of plant cell types including cells of the valve margin or dehiscence zone. A SHATTERPROOF1 or SHATTERPROOF2 (SHP1 and SHP2, also designated as AGL1 and AGL5, repectively) regulatory element, for example, which confers selective expression in ovules and placenta as well as in the dehiscence zone, is a dehiscence zone-selective regulatory element as defined herein. Similarly, an IND1 regulatory element also confers selective expression in the dehiscence zone. A dehiscence zone-selective regulatory element generally is distinguished from other regulatory elements by conferring selective expression in the valve margin or dehiscence zone without conferring expression throughout the adjacent carpel valves.

It is understood that limited modifications can be made without destroying the biological function of a regulatory element and that such limited modifications can result in dehiscence zone-selective regulatory elements that have substantially equivalent or enhanced function as compared to a wild type IND1 regulatory element. These modifications can be deliberate, as through site-directed mutagenesis, or can be accidental such as through mutation in hosts harboring the regulatory element. All such modified nucleotide sequences are included in the definition of a dehiscence zone-selective regulatory element as long as the ability to confer selective expression in the valve margin or dehiscence zone is substantially retained.

The term "plant" includes whole plants, shoot vegetative organs/structures (e.g. leaves, stems and tubers), roots, flowers and floral organs/structures (e.g. bracts, sepals, petals, stamens, carpels, anthers and ovules), seed (including embryo, endosperm, and seed coat) and fruit (the mature ovary), plant tissue (e.g. vascular tissue, ground tissue, and the like) and cells (e.g. guard cells, egg cells, trichomes and the like), and progeny of same. The class of plants that can be used in the method of the invention is generally as broad as the class of higher and lower plants amenable to transformation techniques, including angiosperms (monocotyledonous and dicotyledonous plants), gymnosperms, ferns, and multicellular algae. It includes plants of a variety of ploidy levels, including aneuploid, polyploid, diploid, haploid and hemizygous.

The term "seed plant" means an angiosperm or gymnosperm. An angiosperm is a seed-bearing plant whose seeds are borne in a mature ovary (fruit). An angiosperm commonly is recognized as a flowering plant. Angiosperms are divided into two broad classes based on the number of cotyledons, which are seed leaves that generally store or absorb food. Thus, a monocotyledonous angiosperm is an angiosperm having a single cotyledon, whereas a dicotyledonous angiosperm is an angiosperm having two cotyledons. A variety of angiosperms are known including, for example, oilseed plants, leguminous plants, fruit-bearing plants, ornamental flowers, cereal plants and hardwood trees, which general classes are not necessarily exclusive. The skilled artisan will recognize that the methods of the invention can be practiced using these or other angiosperms, as desired. A gymnosperm is a seed-bearing plant with seeds not enclosed in an ovary.

The phrase "host cell" refers to a cell from any organism. Preferred host cells are derived from plants, bacteria, yeast, fungi, insects or other animals. Methods for introducing polynucleotide sequences into various types of host cells are well known in the art.

The term "delayed," as used herein in reference to the timing of seed dispersal in a fruit produced by a non-naturally occurring plant of the invention, means a significantly later time of seed dispersal as compared to the time seeds normally are dispersed from a corresponding plant at the same developmental stage expressing naturally-occurring levels of IND1. Thus, the term "delayed" is used broadly to encompass both seed dispersal that is significantly postponed as compared to the seed dispersal in a corresponding plant, and to seed dispersal that is completely precluded, such that fruits never release their seeds unless there is human or other intervention.

It is recognized that there can be natural variation of the time of seed dispersal within a plant species or variety. However, a "delay" in the time of seed dispersal in a non-naturally occurring plant of the invention readily can be identified by sampling a population of the non-naturally occurring plants and determining that the normal distribution of seed dispersal times is significantly later, on average, than the normal distribution of seed dispersal times in a population of the corresponding plant species or variety that does not contain an exogenous IND1 polynucleotide. Thus, production of non-naturally occurring plants of the invention provides a means to skew the normal distribution of the time of seed dispersal from pollination, such that seeds are dispersed, on average, at least about 1%, 2%, 5%, 10%, 30%, 50%, 100%, 200% or 500% later than in the corresponding plant species that does not contain an exogenous nucleic acid molecule encoding an IND1 gene product.

The term "suppressed" or "decreased" encompasses the absence of IND1 protein in a plant, as well as protein expression that is present but reduced as compared to the level of IND1 protein expression in a wild type plant. Furthermore, the term suppressed refers to IND1 protein expression that is reduced throughout the entire domain of IND1 expression, or to expression that is reduced in some part of the IND1 expression domain, provided that the resulting plant is characterized by delayed seed dispersal. The term "suppressed" also encompasses an amount of IND1 protein that is equivalent to wild type IND1 expression, but where the IND1 protein has a reduced level of activity. As discussed above, IND1 each contain a conserved an basic HLH domain; point mutations or gross deletions within the HLH domain that reduce the DNA-binding activity of IND1 can reduce or destroy the activity of IND1 and, therefore, "suppress" IND1 expression as defined herein. One skilled in the art will recognize that, preferably, IND1 expression is essentially absent in the valve margin of a plant or the IND1 protein is essentially non-functional.

"Increased" or "enhanced" IND1 activity or expression of a IND1 gene refers to an augmented change in IND1 activity. Examples of such increased activity or expression include the following. IND1 activity or expression of the IND1 gene is increased above the level of that in wild-type, non-transgenic control plants (i.e. the quantity of IND1 activity or expression of the IND1 gene is increased). IND1 activity or expression of the IND1 gene is in an organ, tissue or cell where it is not normally detected in wild-type, non-transgenic control plants (i.e. spatial distribution of IND1 activity or expression of the IND1 gene is increased). IND1 activity or expression is increased when IND1 activity or expression of the IND1 gene is present in an organ, tissue or cell for a longer period than in a wild-type, non-transgenic controls (i.e. duration of IND1 activity or expression of the IND1 gene is increased).

A polynucleotide sequence is "heterologous to" a second polynucleotide sequence if it originates from a foreign species, or, if from the same species, is modified by human action from its original form. For example, a promoter operably linked to a heterologous coding sequence refers to a coding sequence from a species different from that from which the promoter was derived, or, if from the same species, a coding sequence which is different from any naturally occurring allelic variants.

A polynucleotide "exogenous to" an individual plant is a polynucleotide which is introduced into the plant, or a predecessor generation of the plant, by any means other than by a sexual cross. An exogenous nucleic acid molecule can have a naturally occurring or non-naturally occurring nucleotide sequence and can be a heterologous nucleic acid molecule derived from a different plant species than the plant into which the nucleic acid molecule is introduced or can be a nucleic acid molecule derived from the same plant species as the plant into which it is introduced. Examples of means by which this can be accomplished are described below, and include *Agrobacterium*-mediated transformation, biolistic methods, electroporation, in planta techniques, and the like.

An "IND1 polynucleotide" is a nucleic acid sequence comprising (or consisting of) a coding region of about 50 to about 4000 nucleotides, sometimes from about 100 to about 3000 nucleotides and sometimes from about 200 to about 600 nucleotides, which hybridizes to SEQ ID NO:1 under stringent conditions (as defined below), or which encodes an IND1 polypeptide or fragment of at least 15 amino acids thereof. IND1 polynucleotides can also be identified by their ability to hybridize under low stringency conditions (e.g., Tm ~40° C.) to nucleic acid probes having the sequence of SEQ ID NO:1. SEQ ID NO:1 is an example of a IND1 polynucleotide.

A "promoter from a IND1 gene" or "IND1 promoter" will typically be about 500 to about 3000 nucleotides in length, usually from about 750 to 2750. Exemplary promoter sequences are shown as SEQ ID NO:3 and SEQ ID NO:4. SEQ ID NO:3 represents the 5' untranslated region of the IND1 and SEQ ID NO:4 represents the 3' untranslated region of IND1. A IND1 promoter can also be identified by its ability to direct expression in the valve margin of fruit. In particular, the Ind1 promoeter directs expression at the valve margin of developing gynoecium just prior to fertilization (stage 13) through the maturation of the fruit (stage 17). The promoter does not provide significant expression in leaf tissue.

An "IND1 polypeptide" is a sequence of about 50 to about 200, sometimes 100 to 190, and preferably 198 amino acid residues encoded by a IND1 polynucleotide. IND1 polypeptides are characterized by the presence of an basic helix-loop-helix (HLH) domain which bind specific polynucleotide sequences. For instance amino acid residues ISDDPQTVVARRRRERISEKIR-ILKRIVPGGAKMDTASMLDEAIRYTKFLK (SEQ ID NO:7) represent the HLH domain of the polypeptide shown in SEQ ID NO:2. The HLH domain is known in the art and is shared by other transcription factors including uncharacterized sequences represented by GenBank accession number E1283552 and 2262147 and the gene product, PIF3 (Ni et al. Cell 95:657 (1998)). The HLH domain of IND1 is therefore a DNA binding domain.

As used herein, a homolog of a particular IND1 gene (e.g., SEQ ID NO:1) is a second gene in the same plant type or in a different plant type, which has a polynucleotide sequence of at least 50 contiguous nucleotides which are substantially identical (determined as described below) to a sequence in the first gene. It is believed that, in general, homologs share a common evolutionary past.

A "polynucleotide sequence from" a particular gene is a subsequence or full length polynucleotide sequence of an IND1 gene which, when present in a transgenic plant, has the desired effect. For example, one effect is inhibition of expression of the endogenous gene driving expression of an heterologous polynucleotide. A full length sequence of a particular gene disclosed here may contain about 95%, usually at least about 98% of an entire sequence shown in the Sequence Listing, below.

The term "reproductive tissues" as used herein includes fruit, ovules, seeds, pollen, pistols, flowers, or any embryonic tissue.

An "expression cassette" refers to a nucleic acid construct, which when introduced into a host cell, results in transcription and/or translation of a RNA or polypeptide, respectively. Antisense or sense constructs that are not or cannot be translated are expressly included by this definition.

In the case of both expression of transgenes and inhibition of endogenous genes (e.g., by antisense, or sense suppression) one of skill will recognize that the inserted polynucleotide sequence need not be identical and may be "substantially identical" to a sequence of the gene from which it was derived. As explained below, these variants are specifically covered by this term.

In the case where the inserted polynucleotide sequence is transcribed and translated to produce a functional polypeptide, one of skill will recognize that because of codon degeneracy a number of polynucleotide sequences will encode the same polypeptide. These variants are specifically covered by the term "polynucleotide sequence from" a particular valve-margin gene, such as IND1. In addition, the term specifically includes sequences (e.g., full length sequences) substantially identical (determined as described below) with a IND1 gene sequence and that encode proteins that retain the function of a IND1 polypeptide.

In the case of polynucleotides used to inhibit expression of an endogenous gene, the introduced sequence need not be perfectly identical to a sequence of the target endogenous gene. The introduced polynucleotide sequence will typically be at least substantially identical (as determined below) to the target endogenous sequence.

Two nucleic acid sequences or polypeptides are said to be "identical" if the sequence of nucleotides or amino acid residues, respectively, in the two sequences is the same when aligned for maximum correspondence as described below. The term "complementary to" is used herein to mean that the sequence is complementary to all or a portion of a reference polynucleotide sequence.

Optimal alignment of sequences for comparison may be conducted by the local homology algorithm of Smith and Waterman Add. APL. Math. 2:482 (1981), by the homology alignment algorithm of Needle man and Wunsch J. Mol. Biol. 48:443 (1970), by the search for similarity method of Pearson and Lipman Proc. Natl. Acad. Sci. (U.S.A.) 85: 2444 (1988), by computerized implementations of these algorithms (GAP, BESTFIT, BLAST, FASTA, and TFASTA in the Wisconsin Genetics Software Package, Genetics Computer Group (GCG), 575 Science Dr., Madison, Wis.), or by inspection.

"Percentage of sequence identity" is determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

The term "substantial identity" of polynucleotide sequences means that a polynucleotide comprises a sequence that has at least 25% sequence identity. Alternatively, percent identity can be any integer from 25% to 100%. More preferred embodiments include at least: 25%, 30%, 35%, 40%, 45%, 50%, 55%, 60%, 65%, 70%, 75%, 80%, 85%, 90%, 95%, or 99% compared to a reference sequence using the programs described herein; preferably BLAST using standard parameters, as described below. Accordingly, IND1 sequences of the invention include nucleic acid sequences that have substantial identity to SEQ ID NO:1. IND1 sequences of the invention also include polypeptide sequences having substantial identify to SEQ ID NO:2. One of skill will recognize that these values can be appropriately adjusted to determine corresponding identity of proteins encoded by two nucleotide sequences by taking into account codon degeneracy, amino acid similarity, reading frame positioning and the like. Substantial identity of amino acid sequences for these purposes normally means sequence identity of at least 40%. Preferred percent identity of polypeptides can be any integer from 40% to 100%. More preferred embodiments include at least 40%, 45%, 50%, 55%, 60%, 65%, 70%, 75%, 80%, 85%, 90%, 95%, or 99%. Most preferred embodiments include 61%, 62%, 63%, 64%, 65%, 66%, 67%, 68%, 69%, 70%, 71%, 72%, 73%, 74% and 75%. Polypeptides which are "substantially similar" share sequences as noted above except that residue positions which are not identical may differ by conservative amino acid changes. Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Preferred conservative amino acids substitution groups are: valine-leucine-isoleucine, phenylalanine-tyrosine, lysine-arginine, alanine-valine, aspartic acid-glutamic acid, and asparagine-glutamine.

Another indication that nucleotide sequences are substantially identical is if two molecules hybridize to each other, or a third nucleic acid, under stringent conditions. Stringent conditions are sequence dependent and will be different in different circumstances. Generally, stringent conditions are selected to be about 5° C. lower than the thermal melting point (Tm) for the specific sequence at a defined ionic strength and pH. The Tm is the temperature (under defined ionic strength and pH) at which 50% of the target sequence hybridizes to a perfectly matched probe. Typically, stringent conditions will be those in which the salt concentration is about 0.02 molar at pH 7 and the temperature is at least about 60° C.

In the present invention, mRNA encoded by IND1 genes of the invention can be identified in Northern blots under stringent conditions using cDNAs of the invention or fragments of at least about 100 nucleotides. For the purposes of this disclosure, stringent conditions for such RNA-DNA hybridizations are those which include at least one wash in 0.2×SSC at 63° C. for 20 minutes, or equivalent conditions. Genomic DNA or cDNA comprising genes of the invention can be identified using the same cDNAs (or fragments of at least about 100 nucleotides) under stringent conditions, which for purposes of this disclosure, include at least one wash (usually 2) in 0.2× SSC at a temperature of at least about 50° C., usually about 55° C., for 20 minutes, or equivalent conditions.

DETAILED DESCRIPTION

I. Introduction

Figure 1:
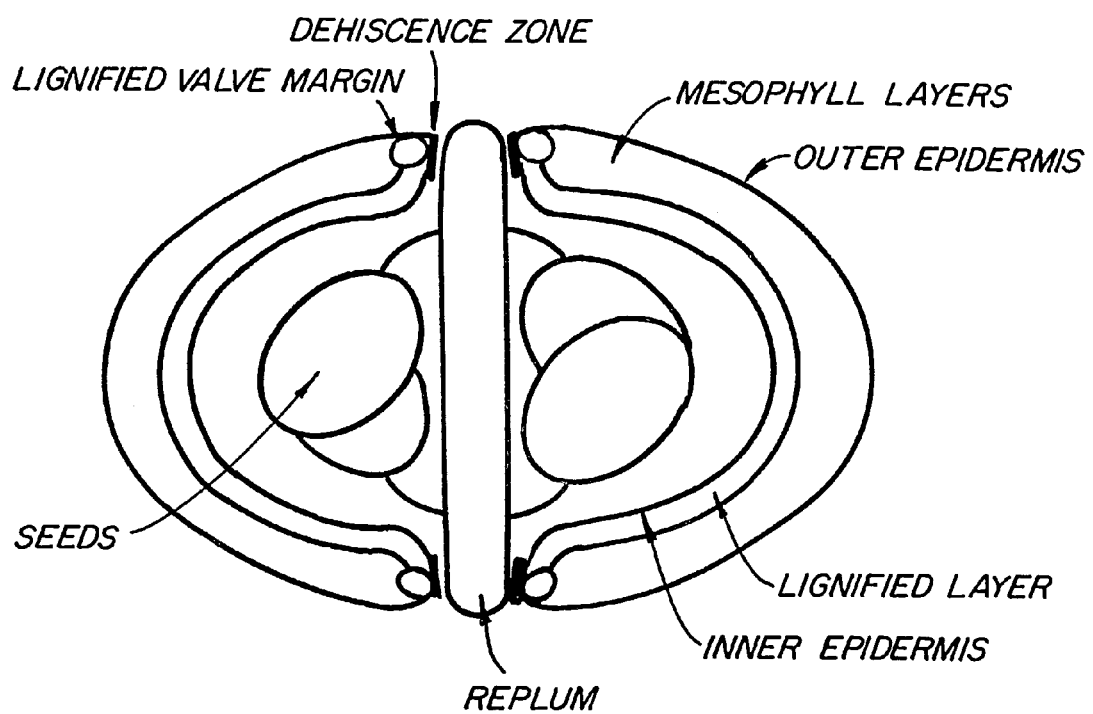
FIG. 1 illustrates the cell types of the *Arabidopsis* fruit at maturity.

The present invention provides methods of modulating fruit development in plants. In particular, the invention provides methods of delaying or preventing fruit dehiscence by suppressing expression of an bHLH gene such as IND1 in a plant. The invention also provides transgenic plants comprising various polynucleotides encoding an bHLH polypeptide such as IND1.

The present invention relates to the previous discovery that an agl1 agl5 double mutant plant has a delayed seed dispersal phenotype (Liljegren et al., *Nature* 404:766–770 (2000)). Loss-of-function mutations in the SHP1 and SHP2 genes were produced by disruptive T-DNA insertion and homologous recombination. In the resulting shp1 shp2 double mutant plants, the dehiscence zone failed to develop normally, and the mature fruits did not undergo dehiscence. Thus, SHP1 or SHP2 gene expression is required for development of the dehiscence zone. These results indicate that SHP1 and SHP2 regulate pod dehiscence and that manipulation of SHP1 and SHP2 expression can allow the process of pod shatter to be controlled.

The present invention provides evidence that IND1 is regulated by SHP1 and SHP2 and that expression of IND1 modulates fruit dehiscence. The present invention also provides for methods of delaying fruit dehiscence by suppressing expression of IND1.

The *Arabidopsis* SHP1 and SHP2 genes encode MADS box proteins with 85% identity at the amino acid level. The SHP1 and SHP2 RNA expression patterns are also strikingly similar. In particular, both RNAs are specifically expressed in flowers, where they accumulate in developing carpels. In particular, strong expression of these genes is observed in the outer replum along the valve/replum boundary (Ma et al., supra, 1991; Savidge et al., *The Plant Cell* 7:721–723 (1995); Flanagan et al., *The Plant Journal* 10:343–353 (1996), each of which is incorporated herein by reference). Thus, SHP1 and SHP2 are expressed in the valve margin, at least within the cells of the outer replum.

Generally, the nomenclature and the laboratory procedures in recombinant DNA technology described below are those well known and commonly employed in the art. Standard techniques are used for cloning, DNA and RNA isolation, amplification and purification. Generally enzymatic reactions involving DNA ligase, DNA polymerase, restriction endonucleases and the like are performed according to the manufacturer's specifications. These techniques and various other techniques are generally performed according to Sambrook et al., Molecular Cloning—A Laboratory Manual, 2nd. ed., Cold Spring Harbor Laboratory, Cold Spring Harbor, N.Y., (1989).

This application is related to U.S. application Ser. No. 09/349,677, filed Jul. 8, 1999, which is a divisional application of U.S. application Ser. No. 09/067,800, filed Apr. 28, 1998, which claims the benefit of priority of U.S. Provisional Application No. 60/051,030, filed Jun. 27, 1997, each of which is incorporated by reference in its entirety.

II. Isolation of Nucleic Acids of the Invention

The isolation of sequences from the genes of the invention may be accomplished by a number of techniques. For instance, oligonucleotide probes based on the sequences disclosed here can be used to identify the desired gene in a cDNA or genomic DNA library from a desired plant species. To construct genomic libraries, large segments of genomic DNA are generated by random fragmentation, e.g. using restriction endonucleases, and are ligated with vector DNA to form concatemers that can be <packaged into the appropriate vector. To prepare a library of embryo-specific cDNAs such as IND1, mRNA is isolated from embryos and a cDNA library that contains the gene transcripts is prepared from the mRNA.

The cDNA or genomic library can then be screened using a probe based upon the sequence of a cloned IND1 gene such as the polynucleotides disclosed here. Probes may be used to hybridize with genomic DNA or cDNA sequences to isolate homologous genes in the same or different plant species.

Alternatively, the nucleic acids of interest can be amplified from nucleic acid samples using amplification techniques. For instance, polymerase chain reaction (PCR) technology to amplify the sequences of the genes directly from mRNA, from cDNA, from genomic libraries or cDNA libraries. PCR and other in vitro amplification methods may also be useful, for example, to clone nucleic acid sequences that code for proteins to be expressed, to make nucleic acids to use as probes for detecting the presence of the desired mRNA in samples, for nucleic acid sequencing, or for other purposes.

Appropriate primers and probes for identifying genes such as IND1 from plant tissues are generated from comparisons of the sequences provided herein. For a general overview of PCR see PCR Protocols: A Guide to Methods and Applications. (Innis, M, Gelfand, D., Sninsky, J. and White, T., eds.), Academic Press, San Diego (1990). Appropriate primers for amplification of the genomic region of IND1 or the IND1 cDNA include the following primer pairs: 5'-gatgaaaatggaaaatggtatgtata-3' (SEQ ID NO:8) and 5'-gtcatcagggttgggagttgtg-3' (SEQ ID NO:9). The amplification conditions are typically as follows. Reaction components: 10 mM Tris-HCl, pH 8.3, 50 mM potassium chloride, 1.5 mM magnesium chloride, 0.001% gelatin, 200 $\mu$M dATP, 200 $\mu$M dCTP, 200 $\mu$M dGTP, 200 $\mu$M dTTP, 0.4 $\mu$M primers, and 100 units per ml Taq polymerase. Program: 96 C for 3 min., 30 cycles of 96 C for 45 sec., 50 C for 60 sec., 72 for 60 sec, followed by 72 C for 5 min.

Polynucleotides may also be synthesized by well-known techniques as described in the technical literature. See, e.g., Carruthers et al., Cold Spring Harbor Symp. *Quant. Biol.* 47:411–418 (1982), and Adams et al., *J. Am. Chem. Soc.* 105:661 (1983). Double stranded DNA fragments may then be obtained either by synthesizing the complementary strand and annealing the strands together under appropriate conditions, or by adding the complementary strand using DNA polymerase with an appropriate primer sequence.

The genus of IND1 nucleic acid sequences of the invention includes genes and gene products identified and characterized by analysis using nucleic acid sequences of the invention, including SEQ ID NO:1 and protein sequences of the invention, including SEQ ID NO:2. IND1 sequences of the invention include nucleic acid sequences having substantial identity to SEQ ID NO:1. IND1 sequences of the invention also include polypeptide sequences having substantial identity to SEQ ID NO:2.

III. Use of Nucleic Acids of the Invention

A. Use of Nucleic Acids of the Invention to Inhibit or Suppress Gene Expression

The invention provides methods of modulating fruit dehiscence in a plant by introducing into a plant a recombinant expression cassette comprising a regulatory element operably linked to a HLH polynucleotide such as IND1. The invention also provides methods for delaying seed dispersal in a plant by suppressing expression of a nucleic acid molecule encoding an IND1 gene product. In a transgenic plant of the invention, a nucleic acid molecule, or antisense constructs thereof, encoding an IND1 gene product can be operatively linked to an exogenous regulatory element. The invention provides, for example, a transgenic plant characterized by delayed seed dispersal having an expressed nucleic acid molecule encoding an IND1 gene product, or antisense construct thereof, that is operatively linked to an exogenous constitutive regulatory element. In one embodiment, the invention provides a transgenic plant that is characterized by delayed seed dispersal due to suppression of a nucleic acid molecule encoding an IND1 ortholog. In some preferred embodiments, suppression of IND1 expression results in reduced lignification in valve margin cells. See also, U.S. application Ser. No. 09/339,998, filed on Jun. 25, 1999.

The IND1 sequences prepared as described herein, can be used to prepare expression cassettes useful in a number of techniques, including inhibiting or suppressing expression. A number of methods can be used to inhibit gene expression in plants. For instance, antisense technology can be conveniently used. To accomplish this, a nucleic acid segment from the desired gene is cloned and operably linked to a promoter such that the antisense strand of RNA will be transcribed. The expression cassette is then transformed into plants and the antisense strand of RNA is produced. In plant cells, it has been suggested that antisense RNA inhibits gene expression by preventing the accumulation of mRNA which encodes the enzyme of interest, see, e.g., Sheehy et al., *Proc. Nat. Acad. Sci. USA*, 85:8805–8809 (1988); Pnueli et al., *The Plant Cell* 6:175–186 (1994); and Hiatt et al., U.S. Pat. No. 4,801,340.

The antisense nucleic acid sequence transformed into plants will be substantially identical to at least a portion of the endogenous gene or genes to be repressed. The sequence, however, does not have to be perfectly identical to inhibit expression. Thus, an antisense or sense nucleic acid molecule encoding only a portion of IND1 can be useful for producing a plant in which IND1 expression is suppressed. The vectors of the present invention can be designed such that the inhibitory effect applies to other proteins within a family of genes exhibiting homology or substantial homology to the target gene.

For antisense suppression, the introduced sequence also need not be full length relative to either the primary transcription product or fully processed mRNA. Generally, higher homology can be used to compensate for the use of a shorter sequence. Furthermore, the introduced sequence need not have the same intron or exon pattern, and homology of non-coding segments may be equally effective. Normally, a sequence of between about 30 or 40 nucleotides and about full length nucleotides should be used, though a sequence of at least about 100 nucleotides is preferred, a sequence of at least about 200 nucleotides is more preferred, and a sequence of at least about 500 nucleotides is especially preferred.

Catalytic RNA molecules or ribozymes can also be used to inhibit expression of IND1 genes. It is possible to design ribozymes that specifically pair with virtually any target RNA and cleave the phosphodiester backbone at a specific location, thereby functionally inactivating the target RNA. In carrying out this cleavage, the ribozyme is not itself altered, and is thus capable of recycling and cleaving other molecules, making it a true enzyme. The inclusion of ribozyme sequences within antisense RNAs confers RNA-cleaving activity upon them, thereby increasing the activity of the constructs.

A number of classes of ribozymes have been identified. One class of ribozymes is derived from a number of small circular RNAs that are capable of self-cleavage and replication in plants. The RNAs replicate either alone (viroid RNAs) or with a helper virus (satellite RNAs). Examples include RNAs from avocado sunblotch viroid and the satellite RNAs from tobacco ringspot virus, lucerne transient streak virus, velvet tobacco mottle virus, *solanum nodiflorum* mottle virus and subterranean clover mottle virus. The design and use of target RNA-specific ribozymes is described in Haseloff et al. *Nature,* 334:585–591 (1988).

Another method of suppression is sense suppression (also known as co-suppression). Introduction of expression cassettes in which a nucleic acid is configured in the sense orientation with respect to the promoter has been shown to be an effective means by which to block the transcription of target genes. For an example of the use of this method to modulate expression of endogenous genes see, Napoli et al., *The Plant Cell* 2:279–289 (1990); Flavell, *Proc. Natl. Acad. Sci., USA* 91:3490–3496 (1994); Kooter and Mol, *Current Opin. Biol.* 4:166–171 (1993); and U.S. Pat. Nos. 5,034,323, 5,231,020, and 5,283,184.

Generally, where inhibition of expression is desired, some transcription of the introduced sequence occurs. The effect may occur where the introduced sequence contains no coding sequence per se, but only intron or untranslated sequences homologous to sequences present in the primary transcript of the endogenous sequence. The introduced sequence generally will be substantially identical to the endogenous sequence intended to be repressed. This minimal identity will typically be greater than about 65%, but a higher identity might exert a more effective repression of expression of the endogenous sequences. Substantially greater identity of more than about 80% is preferred, though about 95% to absolute identity would be most preferred. As with antisense regulation, the effect should apply to any other proteins within a similar family of genes exhibiting homology or substantial homology.

For sense suppression, the introduced sequence in the expression cassette, needing less than absolute identity, also need not be full length, relative to either the primary transcription product or fully processed mRNA. This may be preferred to avoid concurrent production of some plants that are overexpressers. A higher identity in a shorter than full length sequence compensates for a longer, less identical sequence. Furthermore, the introduced sequence need not have the same intron or exon pattern, and identity of non-coding segments will be equally effective. Normally, a sequence of the size ranges noted above for antisense regulation is used.

In a preferred embodiment, expression of a nucleic acid of interest can be suppressed by the simultaneous expression of both sense and antisense constructs (Waterhouse et al., *Proc. Natl. Acad. Sci. USA* 95:13959–13964 (1998). See also Tabara et al. *Science* 282:430–431 (1998).

One of skill in the art will recognize that using technology based on specific nucleotide sequences (e.g., antisense or sense suppression technology), families of homologous genes can be suppressed with a single sense or antisense transcript. For instance, if a sense or antisense transcript is designed to have a sequence that is conserved among a family of genes, then multiple members of a gene family can be suppressed. Conversely, if the goal is to only suppress one member of a homologous gene family, then the sense or antisense transcript should be targeted to sequences with the most vairance between family members.

Another means of inhibiting IND1 function in a plant is by creation of dominant negative mutations. In this approach, non-functional, mutant IND1 polypeptides, which retain the ability to interact with wild-type subunits are introduced into a plant. A dominant negative construct also can be used to suppress IND1 expression in a plant. A dominant negative construct useful in the invention generally contains a portion of the complete IND1 coding sequence sufficient, for example, for DNA-binding or for a protein—protein interaction such as a homodimeric or heterodimeric protein—protein interaction but lacking the transcriptional activity of the wild type protein. For example, a carboxy-terminal deletion mutant of AGAMOUS was used as a dominant negative construct to suppress expression of the MADS box gene AGAMOUS (Mizukami et al., *Plant Cell* 8:831–844 (1996)). One skilled in the art understands that, similarly, a dominant negative IND1 construct can be used to suppress IND1 expression in a plant.

B. Use of Nucleic Acids of the Invention to Enhance Gene Expression

Isolated sequences prepared as described herein can also be used to prepare expression cassettes that enhance or increase endogenous IND1 gene expression. Where overexpression of a gene is desired, the desired gene from a different species may be used to decrease potential sense suppression effects. Enhanced expression of IND1 polynucleotides is useful, for example, to produce plants with small fruit.

Any of a number of means well known in the art can be used to increase IND1 activity in plants. Any organ can be targeted, such as shoot vegetative organs/structures (e.g. leaves, stems and tubers), roots, flowers and floral organs/structures (e.g. bracts, sepals, petals, stamens, carpels, anthers and ovules), seed (including embryo, endosperm, and seed coat) and fruit. Alternatively, one or several IND1 genes can be expressed constitutively (e.g., using the CaMV 35S promoter).

One of skill will recognize that the polypeptides encoded by the genes of the invention, like other proteins, have different domains which perform different functions. Thus, the gene sequences need not be full length, so long as the desired functional domain of the protein is expressed. As explained above, IND1 polypeptides carry a bHLH domain, which is capable of binding DNA. Thus, without being bound to any particular theory or mechanism, IND1 is likely to act as a transcriptional modulator.

C. Modification of Endogenous IND1 Genes

Methods for introducing genetic mutations into plant genes and selecting plants with desired traits are well known. For instance, seeds or other plant material can be treated with a mutagenic chemical substance, according to standard techniques. Such chemical substances include, but are not limited to, the following: diethyl sulfate, ethylene imine, ethyl methanesulfonate and N-nitroso-N-ethylurea. Alternatively, ionizing radiation from sources such as, X-rays or gamma rays can be used.

Modified protein chains can also be readily designed utilizing various recombinant DNA techniques well known to those skilled in the art and described for instance, in Sambrook et al., supra. Hydroxylamine can also be used to introduce single base mutations into the coding region of the gene (Sikorski, et al., (1991). *Meth. Enzymol.* 194: 302–318). For example, the chains can vary from the naturally occurring sequence at the primary structure level by amino acid substitutions, additions, deletions, and the like. These modifications can be used in a number of combinations to produce the final modified protein chain.

Alternatively, homologous recombination can be used to induce targeted gene modifications by specifically targeting the IND1 gene in vivo (see, generally, Grewal and Klar, *Genetics* 146: 1221–1238 (1997) and Xuetal., *Genes Dev.* 10: 2411–2422 (1996)). Homologous recombination has been demonstrated in plants (Puchta et al., *Experientia* 50: 277–284 (1994), Swoboda et al., *EMBO J.* 13: 484–489 (1994); Offringa et al., *Proc. Natl. Acad. Sci. USA* 90: 7346–7350 (1993); and Kempin et al. *Nature* 389:802–803 (1997)).

In applying homologous recombination technology to the genes of the invention, mutations in selected portions of an IND1 gene sequences (including 5' upstream, 3' downstream, and intragenic regions) such as those disclosed here are made in vitro and then introduced into the desired plant using standard techniques. Since the efficiency of homologous recombination is known to be dependent on the vectors used, use of dicistronic gene targeting vectors as described by Mountford et al., *Proc. Natl. Acad. Sci. USA* 91: 4303–4307 (1994); and Vaulont et al., *Transgenic Res.* 4: 247–255 (1995) are conveniently used to increase the efficiency of selecting for altered IND1 gene expression in transgenic plants. The mutated gene will interact with the target wild-type gene in such a way that homologous recombination and targeted replacement of the wild-type gene will occur in transgenic plant cells, resulting in suppression of IND1 activity.

Alternatively, oligonucleotides composed of a contiguous stretch of RNA and DNA residues in a duplex conformation with double hairpin caps on the ends can be used. The RNA/DNA sequence is designed to align with the sequence of the target IND1 gene and to contain the desired nucleotide change. Introduction of the chimeric oligonucleotide on an extrachromosomal T-DNA plasmid results in efficient and specific IND1 gene conversion directed by chimeric molecules in a small number of transformed plant cells. This method is described in Cole-Strauss et al., *Science* 273: 1386–1389 (1996) and Yoon et al., *Proc. Natl. Acad. Sci. USA* 93: 2071–2076 (1996).

In other embodiments, the promoters derived from the IND1 genes of the invention can be used to drive expression of heterologous genes in an valve margin-specific manner. Suitable structural genes that could be used for this purpose include genes encoding cytotoxic proteins as discussed below.

Typically, desired promoters are identified by analyzing the 5' sequences of a genomic clone corresponding to the IND1 genes described here. Sequences characteristic of promoter sequences can be used to identify the promoter. Sequences controlling eukaryotic gene expression have been extensively studied. For instance, promoter sequence elements include the TATA box consensus sequence (TATAAT), which is usually 20 to 30 base pairs upstream of the transcription start site. In most instances the TATA box is required for accurate transcription initiation. In plants, further upstream from the TATA box, at positions −80 to −100, there is typically a promoter element with a series of adenines surrounding the trinucleotide G (or T) N G. J. Messing et al., in GENETIC ENGINEERING 1N PLANTS, pp. 221–227 (Kosage, Meredith and Hollaender, eds. (1983)).

A number of methods are known to those of skill in the art for identifying and characterizing promoter regions in plant genomic DNA (see, e.g., Jordano, et al., *Plant Cell,* 1: 855–866 (1989); Bustos, et al., *Plant Cell,* 1:839–854 (1989); Green, et al., *EMBO J.* 7, 4035–4044 (1988); Meier, et al., *Plant Cell,* 3, 309–316 (1991); and Zhang, et al., *Plant Physiology* 110: 1069–1079 (1996)).

IV. Preparation of Recombinant Vectors

To use isolated sequences in the above techniques, recombinant DNA vectors suitable for transformation of plant cells are prepared. Techniques for transforming a wide variety of higher plant species are well known and described in the technical and scientific literature. See, for example, Weising et al. *Ann. Rev. Genet.* 22:421–477 (1988). A DNA sequence coding for the desired polypeptide, for example a cDNA sequence encoding a full length protein, will preferably be combined with transcriptional and translational initiation regulatory sequences which will direct the transcription of the sequence from the gene in the intended tissues of the transformed plant.

For example, for overexpression, a plant promoter fragment may be employed which will direct expression of the gene in all tissues of a regenerated plant. Such promoters are referred to herein as "constitutive" promoters and are active under most environmental conditions and states of development or cell differentiation. Examples of constitutive promoters include the cauliflower mosaic virus (CaMV) 35S transcription initiation region, the 1'- or 2'-promoter derived from T-DNA of *Agrobacterium tumafaciens*, and other transcription initiation regions from various plant genes known to those of skill.

Alternatively, the plant promoter may direct expression of the polynucleotide of the invention in a specific tissue (tissue-specific promoters) or may be otherwise under more precise environmental control (inducible promoters). Examples of tissue-specific promoters under developmental control include promoters that initiate transcription only in certain tissues, such as fruit, seeds, or flowers. As noted above, the promoters from the IND1 genes described here are particularly useful for directing gene expression so that a desired gene product is located in the valve margin of fruit. Other suitable promoters include those from genes such as SHP1 or SHP2 (Savidge, B., Rounsley, S. D., and Yanofsky, M. F. (1995) *Plant Cell* 7: 721–733). Examples of environmental conditions that may affect transcription by inducible promoters include anaerobic conditions, elevated temperature, or the presence of light.

If proper polypeptide expression is desired, a polyadenylation region at the 3'-end of the coding region should be included. The polyadenylation region can be derived from the natural gene, from a variety of other plant genes, or from T-DNA.

The vector comprising the sequences (e.g., promoters or coding regions) from genes of the invention will typically comprise a marker gene that confers a selectable phenotype on plant cells. For example, the marker may encode biocide resistance, particularly antibiotic resistance, such as resistance to kanamycin, G418, bleomycin, hygromycin, or herbicide resistance, such as resistance to chlorosluforon or Basta.

IND1 nucleic acid sequences of the invention are expressed recombinantly in plant cells to enhance and increase levels of endogenous IND1 polypeptides. Alternatively, antisense or other IND1 constructs (described above) are used to suppress IND1 levels of expression. A variety of different expression constructs, such as expression cassettes and vectors suitable for transformation of plant cells can be prepared. Techniques for transforming a wide variety of higher plant species are well known and described in the technical and scientific literature. See, e.g., Weising et al.

*Ann. Rev. Genet.* 22:421–477 (1988). A DNA sequence coding for a IND1 polypeptide, e.g., a cDNA sequence encoding a full length protein, can be combined with cis-acting (promoter) and trans-acting (enhancer) transcriptional regulatory sequences to direct the timing, tissue type and levels of transcription in the intended tissues of the transformed plant. Translational control elements can also be used.

The invention provides an IND1 nucleic acid operably linked to a promoter which, in a preferred embodiment, is capable of driving the transcription of the IND1 coding sequence in plants. The promoter can be, e.g., derived from plant or viral sources. The promoter can be, e.g., constitutively active, inducible, or tissue specific. In construction of recombinant expression cassettes, vectors, transgenics, of the invention, a different promoters can be chosen and employed to differentially direct gene expression, e.g., in some or all tissues of a plant or animal. Typically, as discussed above, desired promoters are identified by analyzing the 5' sequences of a genomic clone corresponding to the IND1 genes described here.

A. Constitutive Promoters

A promoter fragment can be employed which will direct expression of IND1 nucleic acid in all transformed cells or tissues, e.g. as those of a regenerated plant. The term "constitutive regulatory element" means a regulatory element that confers a level of expression upon an operatively linked nucleic molecule that is relatively independent of the cell or tissue type in which the constitutive regulatory element is expressed. A constitutive regulatory element that is expressed in a plant generally is widely expressed in a large number of cell and tissue types. Promoters that drive expression continuously under physiological conditions are referred to as "constitutive" promoters and are active under most environmental conditions and states of development or cell differentiation.

A variety of constitutive regulatory elements useful for ectopic expression in a transgenic plant are well known in the art. The cauliflower mosaic virus 35S (CaMV 35S) promoter, for example, is a well-characterized constitutive regulatory element that produces a high level of expression in all plant tissues (Odell et al., *Nature* 313:810–812 (1985)). The CaMV 35S promoter can be particularly useful due to its activity in numerous diverse plant species (Benfey and Chua, *Science* 250:959–966 (1990); Futterer et al., *Physiol. Plant* 79:154 (1990); Odell et al., supra, 1985). A tandem 35S promoter, in which the intrinsic promoter element has been duplicated, confers higher expression levels in comparison to the unmodified 35S promoter (Kay et al., *Science* 236:1299 (1987)). Other useful constitutive regulatory elements include, for example, the cauliflower mosaic virus 19S promoter; the Figwort mosaic virus promoter; and the nopaline synthase (nos) gene promoter (Singer et al., *Plant Mol. Biol.* 14:433 (1990); An, *Plant Physiol.* 81:86 (1986)).

Additional constitutive regulatory elements including those for efficient expression in monocots also are known in the art, for example, the pEmu promoter and promoters based on the rice Actin-15' region (Last et al., *Theor. Appl. Genet.* 81:581 (1991); Mcelroy et al., *Mol. Gen. Genet.* 231:150 (1991); Mcelroy et al., *Plant Cell* 2:163 (1990)). Chimeric regulatory elements, which combine elements from different genes, also can be useful for ectopically expressing a nucleic acid molecule encoding an IND1 polynucleotide (Comai et al., *Plant Mol. Biol.* 15:373 (1990)).

Other examples of constitutive promoters include the 1'- or 2'-promoter derived from T-DNA of *Agrobacterium tumafaciens* (see, e.g., Mengiste (1997) supra; O'Grady (1995) *Plant Mol. Biol.* 29:99–108); actin promoters, such as the *Arabidopsis* actin gene promoter (see, e.g., Huang (1997) *Plant Mol. Biol.* 1997 33:125–139); alcohol dehydrogenase (Adh) gene promoters (see, e.g., Millar (1996) *Plant Mol. Biol.* 31:897–904); ACT11 from *Arabidopsis* (Huang et al. *Plant Mol. Biol.* 33:125–139 (1996)), Cat3 from *Arabidopsis* (GenBank No. U43147, Zhong et al., *Mol. Gen. Genet.* 251:196–203 (1996)), the gene encoding stearoyl-acyl carrier protein desaturase from *Brassica napus* (Genbank No. X74782, Solocombe et al. *Plant Physiol.* 104:1167–1176 (1994)), GPc1 from maize (GenBank No. X15596, Martinez et al. *J. Mol. Biol.* 208:551–565 (1989)), Gpc2 from maize (GenBank No. U45855, Manjunath et al., *Plant Mol. Biol.* 33:97–112 (1997)), other transcription initiation regions from various plant genes known to those of skill. See also Holtorf *Plant Mol. Biol.* 29:637–646 (1995).

B. Inducible Promoters

Alternatively, a plant promoter may direct expression of the IND1 nucleic acid of the invention under the influence of changing environmental conditions or developmental conditions. Examples of environmental conditions that may effect transcription by inducible promoters include anaerobic conditions, elevated temperature, drought, or the presence of light. Such promoters are referred to herein as "inducible" promoters. For example, the invention incorporates the drought-inducible promoter of maize (Busk (1997) supra); the cold, drought, and high salt inducible promoter from potato (Kirch (1997) *Plant Mol. Biol.* 33:897–909).

Alternatively, plant promoters which are inducible upon exposure to plant hormones, such as auxins, are used to express the nucleic acids of the invention. For example, the invention can use the auxin-response elements E1 promoter fragment (AuxREs) in the soybean (*Glycine max* L.) (Liu (1997) *Plant Physiol.* 115:397–407); the auxin-responsive *Arabidopsis* GST6 promoter (also responsive to salicylic acid and hydrogen peroxide) (Chen (1996) *Plant J.* 10: 955–966); the auxin-inducible parC promoter from tobacco (Sakai (1996) 37:906–913); a plant biotin response element (Streit (1997) *Mol. Plant Microbe Interact.* 10:933–937); and, the promoter responsive to the stress hormone abscisic acid (Sheen (1996) *Science* 274:1900–1902).

Plant promoters which are inducible upon exposure to chemicals reagents which can be applied to the plant, such as herbicides or antibiotics, are also used to express the nucleic acids of the invention. For example, the maize In2-2 promoter, activated by benzenesulfonamide herbicide safeners, can be used (De Veylder (1997) *Plant Cell Physiol.* 38:568–577); application of different herbicide safeners induces distinct gene expression patterns, including expression in the root, hydathodes, and the shoot apical meristem. IND1 coding sequence can also be under the control of, e.g., a tetracycline-inducible promoter, e.g., as described with transgenic tobacco plants containing the *Avena sativa* L. (oat) arginine decarboxylase gene (Masgrau (1997) *Plant J.* 11:465–473); or, a salicylic acid-responsive element (Stange (1997) *Plant J.* 111:1315–1324; Uknes et al., *Plant Cell* 5:159–169 (1993); Bi et al., *Plant J.* 8:235–245 (1995)).

Particularly useful inducible regulatory elements include copper-inducible regulatory elements (Mett et al., *Proc. Natl. Acad. Sci. USA* 90:4567–4571 (1993); Furst et al., *Cell* 55:705–717 (1988)); tetracycline and chlor-tetracycline-inducible regulatory elements (Gatz et al., *Plant J.* 2:397–404 (1992); Roder et al., *Mol. Gen. Genet.* 243:32–38 (1994); Gatz, *Meth. Cell Biol.* 50:411–424 (1995)); ecdysone inducible regulatory elements (Christopherson et al., *Proc. Natl. Acad. Sci. USA* 89:6314–6318 (1992); Kreutzweiser et al., *Ecotoxicol. Environ. Safety* 28:14–24 (1994)); heat shock inducible regulatory elements (Takahashi et al., *Plant Physiol.* 99:383–390 (1992); Yabe et al., *Plant Cell Physiol.* 35:1207–1219 (1994); Ueda et al., *Mol. Gen. Genet.* 250: 533–539 (1996)); and lac operon elements, which are used in combination with a constitutively expressed lac repressor to confer, for example, IPTG-inducible expression (Wilde et al., *EMBO J.* 11:1251–1259 (1992)). An inducible regulatory element useful in the transgenic plants of the invention also can be, for example, a nitrate-inducible promoter derived from the spinach nitrite reductase gene (Back et al., *Plant Mol. Biol.* 17:9 (1991)) or a light-inducible promoter, such as that associated with the small subunit of RuBP carboxylase or the LHCP gene families (Feinbaum et al., *Mol. Gen. Genet.* 226:449 (1991); Lam and Chua, *Science* 248:471 (1990)).

C. Tissue-Specific Promoters

Alternatively, the plant promoter may direct expression of the polynucleotide of the invention in a specific tissue (tissue-specific promoters). Tissue specific promoters are transcriptional control elements that are only active in particular cells or tissues at specific times during plant development, such as in vegetative tissues or reproductive tissues. Promoters from the IND1 genes of the invention are particularly useful for tissue-specific direction of gene expression so that a desired gene product is generated only or preferentially in embryos or seeds, as described below.

Examples of tissue-specific promoters under developmental control include promoters that initiate transcription only (or primarily only) in certain tissues, such as vegetative tissues, e.g., roots or leaves, or reproductive tissues, such as fruit, ovules, seeds, pollen, pistols, flowers, or any embryonic tissue. Reproductive tissue-specific promoters may be, e.g., ovule-specific, embryo-specific, endosperm-specific, integument-specific, seed and seed coat-specific, pollen-specific, petal-specific, sepal-specific, or some combination thereof.

The invention provides a transgenic plant that is characterized by delayed seed dispersal due to expression of a nucleic acid molecule encoding an IND1 gene product, or an antisense construct thereof, operatively linked to a dehiscence zone-selective regulatory element. The dehiscence zone-selective regulatory element can be, for example, an SHP1 regulatory element or SHP2 regulatory element. The SHP1 regulatory element can be derived from the *Arabidopsis* SHP1 genomic sequence disclosed herein as SEQ ID NO:5 and can be, for example, a 5' regulatory sequence or intronic regulatory element. Similarly, the SHP2 regulatory element can be derived from the *Arabidopsis* SHP2 genomic sequence disclosed herein as SEQ ID NO:6 and can be, for example, a 5' regulatory sequence or intronic regulatory element.

A dehiscence zone-selective regulatory element can be derived from a gene that is an ortholog of *Arabidopsis* IND1 and is selectively expressed in the valve margin or dehiscence zone of a seed plant. A dehiscence zone-selective regulatory element can be derived, for example, from an IND1 ortholog of the *Brassicaceae*, such as a *Brassica napus, Brassica oleracea, Brassica campestris, Brassica juncea, Brassica nigra* or *Brassica carinata* IND1 ortholog. A dehiscence zone-selective regulatory element can be derived, for example, from an IND1 canola ortholog. A dehiscence zone-selective regulatory element also can be derived, for example, from a leguminous IND1 ortholog, such as a soybean, pea, chickpea, moth bean, broad bean, kidney bean, lima bean, lentil, cowpea, dry bean, peanut, alfalfa, lucerne, birdsfoot trefoil, clover, stylosanthes, lotononis bainessii, or sainfoin IND1 ortholog.

Dehiscence zone-selective regulatory elements also can be derived from a variety of other genes that are selectively expressed in the valve margin or dehiscence zone of a seed plant. For example, the rapeseed gene RDPG1 is selectively expressed in the dehiscence zone (Petersen et al., *Plant Mol. Biol.* 31:517–527 (1996)). Thus, the RDPG1 promoter or an active fragment thereof can be a dehiscence zone-selective regulatory element as defined herein. Additional genes such as the rapeseed gene SAC51 also are known to be selectively expressed in the dehiscence zone; the SAC51 promoter or an active fragment thereof also can be a dehiscence zone-selective regulatory element of the invention (Coupe et al., *Plant Mol. Biol.* 23:1223–1232 (1993)). The skilled artisan understands that a regulatory element of any such gene selectively expressed in cells of the valve margin or dehiscence zone can be a dehiscence zone-selective regulatory element as defined herein.

Additional dehiscence zone-selective regulatory elements can be identified and isolated using routine methodology. Differential screening strategies using, for example, RNA prepared from the dehiscence zone and RNA prepared from adjacent pod material can be used to isolate cDNAs selectively expressed in cells of the dehiscence zone (Coupe et al., supra, 1993); subsequently, the corresponding genes are isolated using the cDNA sequence as a probe.

Enhancer trap or gene trap strategies also can be used to identify and isolate a dehiscence zone-selective regulatory element of the invention (Sundaresan et al., supra, 1995; Koncz et al., *Proc. Natl. Acad. Sci. USA* 86:8467–8471 (1989); Kertbundit et al., *Proc. Natl. Acad. Sci. USA* 88:5212–5216 (1991); Topping et al., *Development* 112: 1009–1019 (1991)). Enhancer trap elements include a reporter gene such as GUS with a weak or minimal promoter, while gene trap elements lack a promoter sequence, relying on transcription from a flanking chromosomal gene for reporter gene expression. Transposable elements included in the constructs mediate fusions to endogenous loci; constructs selectively expressed in the valve margin or dehiscence zone are identified by their pattern of expression. With the inserted element as a tag, the flanking dehiscence zone-selective regulatory element is cloned using, for example, inverse polymerase chain reaction methodology (see, for example, Aarts et al., *Nature* 363:715–717 (1993); see also, Ochman et al., "Amplification of Flanking Sequences by Inverse PCR," in Innis et al., supra, 1990). The Ac/Ds transposition system of Sundaresan et al., *Genes. Devel.* 9:1797–1810 (1995), can be particularly useful in identifying and isolating a dehiscence zone-selective regulatory element of the invention.

Dehiscence zone-selective regulatory elements also can be isolated by inserting a library of random genomic DNA fragments in front of a promoterless reporter gene and screening transgenic plants transformed with the library for dehiscence zone-selective reporter gene expression. The promoterless vector pROA97, which contains the npt gene and the GUS gene each under the control of the minimal 35S promoter, can be useful for such screening. The genomic library can be, for example, Sau3A fragments of *Arabidopsis thaliana* genomic DNA or genomic DNA from, for example, another Brassicaceae of interest (Ott et al., *Mol. Gen. Genet.* 223:169–179 (1990); Claes et al., *The Plant Journal* 1:15–26 (1991)).

Dehiscence zone-selective expression of a regulatory element of the invention can be demonstrated or confirmed by routine techniques, for example, using a reporter gene and in situ expression analysis. The GUS and firefly luciferase reporters are particularly useful for in situ localization of plant gene expression (Jefferson et al., *EMBO J.* 6:3901 (1987); Ow et al., *Science* 334:856 (1986)), and promoterless vectors containing the GUS expression cassette are commercially available, for example, from Clontech (Palo Alto, Calif.). To identify a dehiscence zone-selective regulatory element of interest such as an IND1 regulatory element, one or more nucleotide portions of the IND1 gene can be generated using enzymatic or PCR-based methodology (Glick and Thompson, supra, 1993; Innis et al., supra, 1990); the resulting segments are fused to a reporter gene such as GUS and analyzed as described above.

Other tissue-specific promoters include seed promoters. Suitable seed-specific promoters are derived from the following genes: MAC1 from maize (Sheridan (1996) *Genetics* 142:1009–1020); Cat3 from maize (GenBank No. L05934, Abler (1993) *Plant Mol. Biol.* 22:10131–1038); vivparous-1 from *Arabidopsis* (Genbank No. U93215); atmyc1 from *Arabidopsis* (Urao (1996) *Plant Mol. Biol.* 32:571–57; Conceicao (1994) *Plant* 5:493–505); napA from *Brassica napus* (GenBank No. J02798, Josefsson (1987) JBL 26:12196–1301); and the napin gene family from *Brassica napus* (Sjodahl (1995) *Planta* 197:264–271).

A variety of promoters specifically active in vegetative tissues, such as leaves, stems, roots and tubers, can also be used to express the IND1 nucleic acids of the invention. For example, promoters controlling patatin, the major storage protein of the potato tuber, can be used, see, e.g., Kim (1994) *Plant Mol. Biol.* 26:603–615; Martin (1997) *Plant J.* 11:53–62. The ORF13 promoter from *Agrobacterium rhizogenes* which exhibits high activity in roots can also be used (Hansen (1997) *Mol. Gen. Genet.* 254:337–343. Other useful vegetative tissue-specific promoters include: the tarin promoter of the gene encoding a globulin from a major taro (*Colocasia esculenta* L. Schott) corm protein family, tarin (Bezerra (1995) *Plant Mol. Biol.* 28:137–144); the curculin promoter active during taro corm development (de Castro (1992) *Plant Cell* 4:1549–1559) and the promoter for the tobacco root-specific gene TobRB7, whose expression is localized to root meristem and immature central cylinder regions (Yamamoto (1991) *Plant Cell* 3:371–382).

Leaf-specific promoters, such as the ribulose biphosphate carboxylase (RBCS) promoters can be used. For example, the tomato RBCS1, RBCS2 and RBCS3A genes are expressed in leaves and light-grown seedlings, only RBCS 1 and RBCS2 are expressed in developing tomato fruits (Meier (1997) *FEBS Lett.* 415:91–95). A ribulose bisphosphate carboxylase promoters expressed almost exclusively in mesophyll cells in leaf blades and leaf sheaths at high levels, described by Matsuoka (1994) *Plant J.* 6:311–319, can be used. Another leaf-specific promoter is the light harvesting chlorophyll a/b binding protein gene promoter, see, e.g., Shiina (1997) *Plant Physiol.* 115:477–483; Casal (1998) *Plant Physiol.* 116:1533–1538. The *Arabidopsis thaliana* myb-related gene promoter (Atmyb5) described by Li (1996) *FEBS Lett.* 379:117–121, is leaf-specific. The Atmyb5 promoter is expressed in developing leaf trichomes, stipules, and epidermal cells on the margins of young rosette and cauline leaves, and in immature seeds. Atmyb5 mRNA appears between fertilization and the 16 cell stage of embryo development and persists beyond the heart stage. A leaf promoter identified in maize by Busk (1997) *Plant J.* 11:1285–1295, can also be used.

Another class of useful vegetative tissue-specific promoters are meristematic (root tip and shoot apex) promoters. For example, the "SHOOTMERISTEMLESS" and "SCARECROW" promoters, which are active in the developing shoot or root apical meristems, described by Di Laurenzio (1996) *Cell* 86:423–433; and, Long (1996) *Nature* 379: 66–69; can be used. Another useful promoter is that which controls the expression of 3-hydroxy-3methylglutaryl coenzyme A reductase HMG2 gene, whose expression is restricted to meristematic and floral (secretory zone of the stigma, mature pollen grains, gynoecium vascular tissue, and fertilized ovules) tissues (see, e.g., Enjuto (1995) *Plant Cell.* 7:517–527). Also useful are kn1-related genes from maize and other species which show meristem-specific expression, see, e.g., Granger (1996) *Plant Mol. Biol.* 31:373–378; Kerstetter (1994) *Plant Cell* 6:1877–1887; Hake (1995) *Philos. Trans. R. Soc. Lond. B. Biol. Sci.* 350:45–51. For example, the *Arabidopsis thaliana* KNAT1 promoter. In the shoot apex, KNAT1 transcript is localized primarily to the shoot apical meristem; the expression of KNAT1 in the shoot meristem decreases during the floral transition and is restricted to the cortex of the inflorescence stem (see, e.g., Lincoln (1994) *Plant Cell* 6:1859–1876).

One of skill will recognize that a tissue-specific promoter may drive expression of operably linked sequences in tissues other than the target tissue. Thus, as used herein a tissue-specific promoter is one that drives expression preferentially in the target tissue, but may also lead to some expression in other tissues as well.

In another embodiment, a IND1 nucleic acid is expressed through a transposable element. This allows for constitutive, yet periodic and infrequent expression of the constitutively active polypeptide. The invention also provides for use of tissue-specific promoters derived from viruses which can include, e.g., the tobamovirus subgenomic promoter (Kumagai (1995) *Proc. Natl. Acad. Sci. USA* 92:1679–1683; the rice tungro bacilliform virus (RTBV), which replicates only in phloem cells in infected rice plants, with its promoter which drives strong phloem-specific reporter gene expression; the cassaya vein mosaic virus (CVMV) promoter, with highest activity in vascular elements, in leaf mesophyll cells, and in root tips (Verdaguer (1996) *Plant Mol. Biol.* 31:1129–1139).

V. Production of Transgenic Plants

DNA constructs of the invention may be introduced into the genome of the desired plant host by a variety of conventional techniques. For example, the DNA construct may be introduced directly into the genomic DNA of the plant cell using techniques such as electroporation and microinjection of plant cell protoplasts, or the DNA constructs can be introduced directly to plant tissue using ballistic methods, such as DNA particle bombardment. Alternatively, the DNA constructs may be combined with suitable T-DNA flanking regions and introduced into a conventional *Agrobacterium tumefaciens* host vector. The virulence functions of the *Agrobacterium tumefaciens* host will direct the insertion of the construct and adjacent marker into the plant cell DNA when the cell is infected by the bacteria.

Microinjection techniques are known in the art and well described in the scientific and patent literature. The introduction of DNA constructs using polyethylene glycol precipitation is described in Paszkowski et al. *Embo J.* 3:2717–2722 (1984). Electroporation techniques are described in Fromm et al. *Proc. Natl. Acad. Sci. USA* 82:5824 (1985). Ballistic transformation techniques are described in Klein et al. *Nature* 327:70–73 (1987).

*Agrobacterium tumefaciens*-mediated transformation techniques, including disarming and use of binary vectors, are well described in the scientific literature. See, for example Horsch et al. *Science* 233:496–498 (1984), and Fraley et al. *Proc. Natl. Acad. Sci. USA* 80:4803 (1983).

Transformed plant cells which are derived by any of the above transformation techniques can be cultured to regenerate a whole plant which possesses the transformed genotype and thus the desired phenotype such as seedlessness. Such regeneration techniques rely on manipulation of certain phytohormones in a tissue culture growth medium, typically relying on a biocide and/or herbicide marker which has been introduced together with the desired nucleotide sequences. Plant regeneration from cultured protoplasts is described in Evans et al., Protoplasts Isolation and Culture, Handbook of Plant Cell Culture, pp. 124–176, MacMillilan Publishing Company, New York, 1983; and Binding, Regeneration of Plants, Plant Protoplasts, pp. 21–73, CRC Press, Boca Raton, 1985. Regeneration can also be obtained from plant callus, explants, organs, or parts thereof. Such regeneration techniques are described generally in Klee et al. *Ann. Rev. of Plant Phys.* 38:467–486 (1987).

The nucleic acids of the invention can be used to confer desired traits on essentially any plant. Thus, the invention has use over a broad range of plants, including species from the genera Asparagus, Atropa, Avena, Brassica, Citrus, Citrullus, Capsicum, Cucumis, Cucurbita, Daucus, Fragaria, Glycine, Gossypium, Helianthus, Heterocallis, Hordeum, Hyoscyamus, Lactuca, Linum, Lolium, Lycopersicon, Malus, Manihot, Majorana, Medicago, Nicotiana, Oryza, Panieum, Pannesetum, Persea, Pisum, Pyrus, Prunus, Raphanus, Secale, Senecio, Sinapis, Solanum, Sorghum, Trigonella, Triticum, Vitis, Vigna, and, Zea. A useful plant of the invention can be a dehiscent seed plant, and a particularly useful plant of the invention can be a member of the Brassicaceae, such as rapeseed, or a member of the Fabaceae, such as a soybean, pea, lentil or bean plant.

In one embodiment, the invention provides a dehiscent seed plant that is characterized by delayed seed dispersal due to suppressed expression of a nucleic acid molecule encoding an IND1 gene product in the dehiscent seed plant. As used herein, the term "dehiscent seed plant" means a plant that produces a dry dehiscent fruit, which has fruit walls that open to permit escape of the seeds contained therein. Dehiscent fruits commonly contain several seeds and include the fruits known, for example, as legumes, capsules and siliques.

In one embodiment, the invention provides a plant that is characterized by delayed seed dispersal due to suppressed expression of a nucleic acid molecule encoding an IND1 gene product, where the plant is a member of the *Brassicaceae*. The *Brassicaceae*, commonly known as the Brassicas, are a diverse group of crop plants with great economic value worldwide (see, for example, Williams and Hill, *Science* 232:1385–1389 (1986), which is incorporated herein by reference). The *Brassicaceae* produce seed oils for margarine, salad oil, cooking oil, plastic and industrial uses; condiment mustard; leafy, stored, processed and pickled vegetables; animal fodders and green manures for soil rejuvenation. A particularly useful non-naturally occurring *Brassica* plant of the invention is the oilseed plant canola.

There are six major *Brassica* species of economic importance, each containing a range of plant forms. *Brassica napus* includes plants such as the oilseed rapes and rutabaga. *Brassica oleracea* are the cole crops such as cabbage, cauliflower, kale, kohlrabi and Brussels sprouts. *Brassica campestris* (*Brassica rapa*) includes plants such as Chinese cabbage, turnip and pak choi. *Brassica juncea* includes a variety of mustards; *Brassica nigra* is the black mustard; and *Brassica carinata* is Ethiopian mustard. The skilled artisan understands that any member of the *Brassicaceae* can be modified as disclosed herein to produce a non-naturally occurring *Brassica* plant characterized by delayed seed dispersal.

In a second embodiment, the invention provides a plant that is characterized by delayed seed dispersal due to suppressed expression of a nucleic acid molecule encoding an IND1 gene product, where the plant is a member of the *Fabaceae*. The *Fabaceae*, which are commonly known as members of the pea family, are plants that produce a characteristic dry dehiscent fruit known as a legume. The legume is derived from a single carpel and dehisces along the suture of the carpel margins and along the median vein. The *Fabaceae* encompass both grain legumes and forage legumes. Grain legumes include, for example, soybean (glycine), pea, chickpea, moth bean, broad bean, kidney bean, lima bean, lentil, cowpea, dry bean and peanut. Forage legumes include alfalfa, lucerne, birdsfoot trefoil, clover, stylosanthes species, *lotononis bainessii* and sainfoin. The skilled artisan will recognize that any member of the *Fabaceae* can be modified as disclosed herein to produce a non-naturally occurring plant of the invention characterized by delayed seed dispersal.

A non-naturally occurring plant of the invention characterized by delayed seed dispersal also can be a member of the plant genus *Cuphea* (family *Lythraceae*). A *Cuphea* plant is particularly valuable since *Cuphea* oilseeds contain industrially and nutritionally important medium-chain fatty acids, especially lauric acid, which is currently supplied only by coconut and palm kernel oils.

A non-naturally occurring plant of the invention also can be, for example, one of the monocotyledonous grasses, which produce many of the valuable small-grain cereal crops of the world. Suppression of IND1 expression as described above, can be useful in generating a non-naturally occurring small grain cereal plant, such as a barley, wheat, oat, rye, orchard grass, guinea grass, sorghum or turf grass plant characterized by delayed seed dispersal.

VI. Additional Modifications that Modulate Seed Dispersal

It should be recognized that a plant of the invention, which contains an exogenous IND1 polynucleotide, also can contain one or more additional modifications, including naturally and non-naturally occurring modifications, that can modulate the delay in seed dispersal. For example, the plant hormone ethylene promotes fruit dehiscence, and modified expression or activity of positive or negative regulators of the ethylene response can be included in a plant of the invention (see, generally, Meakin and Roberts, *J. Exp. Botany* 41:1003–1011 (1990); Ecker, *Science* 268:667–675 (1995); Chao et al., *Cell* 89:1133–1144 (1997)).

Mutations in positive regulators of the ethylene response show a reduction or absence of responsiveness to treatment with exogenous ethylene. *Arabidopsis* mutations in positive regulators of the ethylene response include mutations in etr, which inactivate a histidine kinase ethylene receptor (Bleeker et al., *Science* 241:1086–1089 (1988); Schaller and Bleeker, *Science* 270:1809–1811 (1995)); ers (Hua et al., *Science* 269:1712–1714 (1995)); ein2 (Guzman and Ecker, *Plant Cell* 2:513 (1990)); ein3 (Rothenberg and Ecker, *Sem. Dev. Biol. Plant Dev. Genet.* 4:3–13 (1993); Kieber and Ecker, *Trends Genet.* 9:356–362 (1993)); ain1 (van der Straeten et al., *Plant Physiol.* 102:401–408 (1993)); eti (Harpham et al., *An. Bot.* 68:55 (1991)) and ein4, ein5, ein6, and ein7 (Roman et al., *Genetics* 139: 1393–1409 (1995)). Similar genetic functions are found in other plant species; for example, the never-ripe mutation corresponds to etr and confers ethylene insensitivity in tomato (Lanahan et al., *The Plant Cell* 6:521–530 (1994); Wilkinson et al., *Science* 270:1807–1809 (1995)). A plant of the invention can include a modification that results in altered expression or activity of any such positive regulator of the ethylene response. A mutation in a positive regulator, for example, can be included in a plant of the invention and can modify the delay in seed dispersal in such plants, for example, by further postponing the delay in seed dispersal.

Mutations in negative regulators of the ethylene response display ethylene responsiveness in the absence of exogenous ethylene. Such mutations include those relating to ethylene overproduction, for example, the eto1, eto2, and eto3 mutants, and those relating to constitutive activation of the ethylene signalling pathway, for example, mutations in CTR1, a negative regulator with sequence similarity to the Raf family of protein kinases (Kieber et al., *Cell* 72:427–441 (1993), which is incorporated herein by reference). A plant of the invention can include a modification that results in altered expression or activity of any such negative regulator of the ethylene response. A mutation resulting in ethylene responsiveness in the absence of exogenous ethylene, for example, can be included in a non-naturally occurring plant of the invention and can modify, for example, diminish, the delay in seed dispersal.

Fruit morphological mutations also can be included in a plant of the invention. Such mutations include those in carpel identity genes such as *AGAMOUS* (Bowman et al., supra, 1989; Yanofsky et al., supra, 1990) and in genes required for normal fruit development such as ETTIN, CRABS CLAW, SPATULA, AGL8 and TOUSLED (Sessions et al., *Development* 121:1519–1532 (1995); Alvarez and Smyth, *Flowering Newsletter* 23:12–17 (1997); and Roe et al., *Cell* 75:939–950 (1993)). Thus, it is understood that a plant of the invention can include one or more additional genetic modifications, which can diminish or enhance the delay in seed dispersal.

VII. Expression of Cytotoxic Gene Products

The present invention also provides a recombinant nucleic acid molecule that includes a dehiscence zone-selective regulatory element operatively linked to a nucleic acid molecule encoding a cytotoxic gene product. Further provided herein is a plant of the invention that is characterized by delayed seed dispersal due to expression of a recombinant nucleic acid molecule having a dehiscence zone—selective regulatory element operatively linked to a nucleic acid molecule encoding a cytotoxic gene product.

A cytotoxic gene product is a gene product that causes the death of the cell in which it is expressed and, preferably, does not result in the death of cells other than the cell in which it is expressed. Thus, expression of a cytotoxic gene product from a dehiscence zone-selective regulatory element can be used to ablate the dehiscence zone without disturbing neighboring cells of the replum or valve. A variety of cytotoxic gene products useful in seed plants are known in the art including, for example, diphtheria toxin A chain polypeptides; RNase T1; Barnase RNase; ricin toxin A chain polypeptides; and herpes simplex virus thymidine kinase (tk) gene products. While the diphtheria toxin A chain, RNase T1 and Barnase RNase are preferred cytotoxic gene products, the skilled person recognizes that these, or other cytotoxic gene products can be used with a dehiscence zone-selective regulatory element to generate a non-naturally occurring seed plant characterized by delayed seed dispersal.

Diphtheria toxin is the naturally occurring toxin of Cornebacterium diphtheriae, which catalyzes the ADP-ribosylation of elongation factor 2, resulting in inhibition of protein synthesis and consequent cell death (Collier, *Bacteriol. Rev.* 39:54–85 (1975)). A single molecule of the fully active toxin is sufficient to kill a cell (Yamaizumi et al., *Cell* 15:245–250 (1978)). Diphtheria toxin has two subunits: the diphtheria toxin B chain directs internalization to most eukaryotic cells through a specific membrane receptor, whereas the A chain encodes the toxic catalytic domain. The catalytic DT-A chain does not include a signal peptide and is not secreted. Further, any DT-A released from dead cells in the absence of the diphtheria toxin B chain is precluded from cell attachment. Thus, DT-A is cell autonomous and directs killing only of the cells in which it is expressed without apparent damage to neighboring cells. The DT-A expression cassette of Palmiter et al., which contains the 193 residues of the A chain engineered with a synthetic ATG and lacking the native leader sequence, is particularly useful in the seed plants of the invention (Palmiter et al., *Cell* 50:435–443 (1987); Greenfield et al., *Proc. Natl. Acad. Sci., USA* 80:6853–6857 (1983)).

RNase T1 of *Aspergillus oryzae* and Barnase RNase of *Bacillus* amylolique-faciens also are cytotoxic gene products useful in the seed plants of the invention (Thorsness and Nasrallah, *Methods in Cell Biology* 50:439–448 (1995)). Barnase RNase may be more generally toxic to plants than RNase T1 and, thus, is preferred in the methods of the invention.

Ricin, a ribosome-inactivating protein produced by castor bean seeds, also is a cytotoxic gene product useful in a non-naturally occurring seed plant of the invention. The ricin toxin A chain polypeptide can be used to direct cell-specific ablation as described, for example, in Moffat et al., *Development* 114:681–687 (1992). Plant ribosomes are variably susceptible to the plant-derived ricin toxin. The skilled person understands that the toxicity of ricin depends is variable and should be assessed for toxicity in the seed plant species of interest (see Olsnes and Pihl, Molecular Action of Toxins and Viruses, pages 51–105, Amsterdam: Elsevier Biomedical Press (1982)).

EXAMPLES

The following examples are offered to illustrate, but no to limit the claimed invention.

Example 1

The GT140 valve margin marker (Sundaresan, V., et al. *Genes Dev.* 9, 1797–1810 (1995)) is expressed at the valve margin of the developing gynoecium just prior to fertilization (stage 13) and this pattern persists in the mature fruit (stage 17). As expression of this marker is largely absent from the valve margins of shp1 shp2 indehiscent fruits (Liljegren, S. J., Ditta, G. S., Eshed, Y., Savidge, B., Bowman, J. L., and Yanofsky, M. F. *Nature*, in press), it was expected that the gene corresponding to this marker might also be involved in valve margin development and be required for fruit dehiscence.

To isolate flanking genomic sequence from the GT140 marker insertion site, TAIL/PCR was performed as previously described (Tsugeki, R., et al. *Plant J.* 10, 479–489 (1996)). Subsequent sequencing of the isolated PCR products demonstrated that they correspond to a fully sequenced BAC from chromosome 4, available in the public database as part of the *Arabidopsis* Genome Initiative. The GT140 insertion is located between two genes, one encoding a predicted basic helix-loop-helix (bHLH) transcription factor and the other representing a novel gene.

Through several lines of subsequent investigation, it was confirmed that the bHLH transcription factor (herein referred to as IND1 as noted below) was the relevant gene (SEQ ID NO:1). Promoter/enhancer::GUS fusions of the IND1 gene were introduced into wild-type plants and found to express GUS in an identical pattern to that of the GT140 marker line. Interestingly, approximately 25% of the transgenic lines failed to express significant GUS activity and displayed an indehiscent phenotype. The most likely explanation of these results is that the IND1::GUS fusions, as well as of the endogenous IND1 gene, were cosuppressed. Subsequent RNA blotting confirmed a down regulation of the IND1 gene in these lines, and further RNA blotting showed, as expected, a decrease in IND1 gene expression in shp1 shp2 fruits.

In parallel to the studies of the GT140 valve margin marker described above, screens for *Arabidopsis* mutants producing indehiscent fruits were also carried out. Besides obtaining additional alleles of SHP1 and SHP2 through EMS mutagenesis of shp2-1 and shp1-1 seed stocks, indehiscent mutants that were not allelic to either SHP1 or SHP2, respectively were also obtained. Because the GT140 studies suggested the possibility that one or more of these indehiscent mutants might correspond to the IND1 gene, IND1 from several of these mutants was cloned and sequenced. Four alleles represent independent mutant alleles of IND1. The strongest allele, ind1-2, contains a single nucleotide deletion within codon 55 that results in a frameshift and production of a truncated protein of 64 rather than 198 amino acids. The ind1-1 and ind1-3 alleles contain nucleotide substitutions at codons 141 and 128 that changes a leucine amino acid to a phenylalanine and an arginine to a histidine, respectively. These affected amino acids are both at conserved positions within the bHLH domain. The ind1-4 allele contains a nucleotide substitution at codon 92 that changes a glutamine to a stop codon, causing production of a truncated protein of 91 amino acids. Since inactivation of this bHLH transcription factor prevents fruit dehiscence, the gene is referred to as INDEHISCENT1 (IND1) and the mutant as, ind1. To date, ind1 represents the only reported single gene mutation in *Arabidopsis* that specifically blocks fruit dehiscence.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. An expression cassette comprising a promoter operably linked to a heterologous IND1 polynucleotide, or a complement thereof, encoding a polypeptide at least 95% identical to SEQ ID NO:2, wherein introduction of the expression cassette into a plant to suppress IND1 expression results in a plant with delayed fruit dehiscence.

2. The expression cassette of claim 1, wherein the IND1 polynucleotide comprises positions from about 2765 to about 3361 of SEQ ID NO 1.

3. The expression cassette of claim 1, wherein the promoter is constitutive.

4. The expression cassette of claim 1, wherein the promoter is tissue specific.

5. The expression cassette of claim 4, wherein the promoter is a dehiscence zone specific promoter.

6. A plant comprising a recombinant expression cassette comprising a promoter operably linked to a polynucleotide encoding a polypeptide at least 95% identical to SEQ ID NO:2.

7. The plant of claim 6, wherein the polynucleotide encoding the IND1 polypeptide is operably linked in the antisense orientation to the promoter.

8. The plant of claim 6, wherein the polynucleotide encoding the IND1 polypeptide is operably linked in the sense orientation to the promoter.

9. The plant of claim 8, wherein the polynucleotide sequence further comprises a second polynucleotide sequence encoding the IND1 polypeptide wherein the second polynucleotide is operably linked in the antisense orientation to a second promoter.

10. The plant of claim 6, wherein lignification is reduced in valve margin cells.

11. The plant of claim 6, wherein the promoter is a dehiscence zone-selective regulatory element.

12. A method of delaying fruit dehiscence in a plant, the method comprising suppressing expression of an IND1 nucleic acid in the plant by introducing into the plant a recombinant expression cassette comprising a promoter operably linked to a polynucleotide encoding an IND1 polypeptide at least about 95% identical to SEQ ID NO: 2, wherein the IND1 polypeptide comprises a basic helix-loop-helix (bHLH) domain.

13. The method of claim 12, wherein the IND 1 polypeptide comprises SEQ ID. NO:2.

14. The method of claim 12, wherein the IND1 polynucleotide comprises positions from about 2765 to about 3361 of SEQ ID NO: 1.

15. The method of claim 12, wherein the IND1 polynucleotide comprises SEQ ID NO: 1.

16. The method of claim 12, wherein the polynucleotide encoding the IND1 polypeptide is operably linked in the antisense orientation to the promoter.

17. The method of claim 12, wherein the polynucleotide encoding the IND1 polypeptide is operably linked in the sense orientation to the promoter.

18. The method of claim 17, wherein the polynucleotide further comprises a second polynucleotide sequence encoding the IND1 polypeptide wherein the second polynucleotide is operably linked in the antisense orientation to a second promoter.

19. The method of claim 12, wherein lignification is reduced in valve margin cells.

20. The method of claim 12, wherein the promoter is a dehiscence zone-selective regulatory element.

21. The method of claim 12, wherein the recombinant expression cassette is introduced into the plant using *Agrobacterium*.

22. An expression cassette comprising a heterologous promoter operably linked to polynucleotide, or a complement thereof, wherein the polynucleotide comprises at least 200 contiguous nucleotides from positions 2765 to 3361 of SEQ ID NO:1, wherein introduction of the expression cassette into a plant to suppress IND1 expression results in a plant with delayed fruit dehiscence.

23. The expression cassette of claim 22, wherein the polynucleotide comprises at least 500 contiguous nucleotides from positions 2765 to 3361 of SEQ ID NO:1.

24. The expression cassette of claim 22, wherein the polynucleotide is in a sense orientation with the promoter.

25. The expression cassette of claim 22, wherein the promoter is constitutive.

26. The expression cassette of claim 22, wherein the promoter is tissue specific.

27. The expression cassette of claim 22, wherein the promoter is a dehiscence zone specific promoter.

28. The method of claim 12, wherein the plant is a *Brassica* species.

29. A plant comprising the expression cassette of claim 22.

30. The plant of claim 29, wherein the plant is a *Brassica* species.

31. A method of delaying fruit dehiscence in a plant, the method comprising suppressing expression of an IND1 nucleic acid in the plant by introducing into the plant an expression cassette comprising a heterologous promoter operably linked to polynucleotide, or a complement thereof, wherein the polynucleotide comprises at least 200 contiguous nucleotides from positions 2765 to 3361 of SEQ ID NO:1.

32. The method of claim 31, wherein the polynucleotide comprises at least 500 contiguous nucleotides from positions 2765 to 3361 of SEQ ID NO:1.

33. The method of claim 31, wherein the polynucleotide is in an antisense orientation with the promoter.

34. The method of claim 31, wherein the polynucleotide is in a sense orientation with the promoter.

35. The method of claim 34, wherein the polynucleotide further comprises a second polynucleotide sequence comprising at least 200 contiguous nucleotides from positions 2765 to 3361 of SEQ ID NO:1, wherein the second polynucleotide is operably linked to a second promoter in the antisense orientation.

36. The method of claim 31, wherein the promoter is constitutive.

37. The method of claim 31, wherein the promoter is tissue specific.

38. The method of claim 31, wherein the promoter is a dehiscence zone specific promoter.

39. The method of claim 31, wherein the plant is a *Brassica* species.

40. The method of claim 31, wherein lignification is reduced in valve margin cells.

41. The method of claim 31, wherein the recombinant expression cassette is introduced into the plant using *Agrobacterium*.

42. The expression cassette of claim 22, wherein the polynucleotide is in an antisense orientation with the promoter.

43. The plant of claim 29, wherein the polynucleotide is in a sense orientation with the promoter.

44. The plant of claim 16, wherein the polynucleotide further comprises a second polynucleotide sequence comprising at least 200 contiguous nucleotides from positions 2765 to 3361 of SEQ ID NO:1, wherein the second polynucleotide is operably linked to a second promoter in the antisense orientation.

45. A plant comprising the expression cassette of claim 1.

* * * * *

SEQUENCE LISTING

```
<160> NUMBER OF SEQ ID NOS: 9

<210> SEQ ID NO 1
<211> LENGTH: 3856
<212> TYPE: DNA
<213> ORGANISM: Arabidopsis thaliana
<220> FEATURE:
<223> OTHER INFORMATION: INDEHISCENT1 (IND1) genomic
<221> NAME/KEY: CDS
<222> LOCATION: (2765)..(3361)
<223> OTHER INFORMATION: IND1

<400> SEQUENCE: 1
ctctagacca tctactatcc ggttgttgac ccttaaagct tttgaagact actagaataa      60
tgcaaatacc atatgtccat atccatcctt ttcttttgtt tgaactgaac attctaattt     120
tgtaaaagaa aaaccttat gttaatatca ccgtaggcaa aaaaaatatc tcatcatatt     180
aaatttttat tataagatta tacattctct cgttgtaaga gttactccaa ttgcaagtgt     240
tgtattaact aataaaaagg acgaaagtag gaagcttata attaattgat gttgcatagt     300
actggtatat tgttgatgaa tataacaagt atgaacatta atgcatgaaa cggggtattt     360
tgtcttgaac tcattaaagg caatgtgaaa agaagatgtg aggtctcatt ttgaaaattt     420
atcttctagc tttgtcgatt ttaaatctat gaaatgaacg caacatatag aaatttcatg     480
tggacaacga catttagacg gtatcttaat tagaccgatt aattagtaat atacttatat     540
atataattag tggtgattat aagtttactt atccacttga gaatttaaac aatgggcaat     600
accttaatgt cgaaagaagc cgtccccact tcgtgtaatg agttatgggg gagagatcct     660
gttaaatcgt caaataaaac aacttaagaa ctagaaattg acaccaaaaa tcataaagag     720
aacgttgaag aagtcattta tcgtatccag ctcatatttc ctagctaaga tcaaatcaag     780
```

-continued

```
gccgttgaaa gggcttgtaa gaaaatgtcg aagaaaccgt ggggtttaga agaaagacaa    840
gaaatagaag aacaatgatg ttaaattgcc tattttggtg tataggagtt gtcaaaagag    900
gagagagaga agaaaattag gtcaaaataa tgagcactaa aaatggagac atgtgttgag    960
taactattac aagagcgact tatgcttcct tatggcaatg atatccaaac caaagtgcaa   1020
cgctcctttt ttgccctaat ttcgtaaagt ctctctcctt cttcgtcctt aggaaaaacc   1080
ctagaaattt aatcccttgt tcttgatctt gcttttgag taaccatgat tttgaccaca    1140
cactatttct tctatctttt gtggtctata ggattttgct ttatatgtgt ttcttgtatt   1200
gctccgtacg tacgtatacg aatttaaatg gttataacaa ggtttatata aactagcaca   1260
aatgagtcca tgaaatttgt tagcgaaaaa ggtagaaata tattgagtct ttaaacggca   1320
atatatataa ttttgctgca aaacttagct ttaatcatga tctaatgata ttttctttaa   1380
tttcctttgc caaattaatc acatgcacgg attttggca agttatgtgt cgaattcttc    1440
cattcacaca acactaaact taattagaac tctaggaaat attttaaaat gacaacttta   1500
tcgaaaaaaa tttagttatg aaaacaattc cagaattaaa catgagctat ataatttaag   1560
ataaaatgaa gtaatattga tatgtatgta ataacatatc tgattgcggt aaaaaaaaac   1620
atatctgatt aaattgttca tgcaggccca tgtcactatg atgtcatcac gttttatttt   1680
tcacaataac taatatatat tcaaaaaaat agttttgtca gattaaattt tttttggtgg   1740
tcagctttct ccaacctact aaactagttt ggaatgttct cttctttatt tttcttttc    1800 ttgatttctt atgttttta tttatggaat tttaagacgg attgtttagg tcgtttctct    1860
cttttcttgt tttctaaagt tacttttgta aactcatctc ctcccaatta gacagtcaat   1920
catatagtta tcttttaata tatgtctagt tgataaaaaa aatgaaaaaa tactggtggt   1980
agttctacta atgtttgtgt aaaaaatctg atattatgaa tctaatcaat ttctttgatc   2040
gtataatgtg ggttaaattt agtaattttt tacataaata agaactgtaa tgttgatgta   2100
tattggggaa tcagtatatt agcttgggta actatacttc tggaaatact tgaagattta   2160
actatttgca aaattataat ttagtcccga aaaatacaga cgacgggaca cgacaacata   2220
taagcaggtt tgaatcttgg aaaattttgt atacataacc tatataaata ctaatgttct   2280
ggttgggttc aaaagccttt tcaaaagttc catttttaa attcaaggac attttacata    2340
ggaaataagt tgagtcataa aaaataatgg ttattttgta aggtttttt tttgattaaa    2400 acgcacatat taagaagtta gttttttttc actaccaaat atcaattaat ttaaaaccat   2460
gcaaccattc ataaaacaat actattaaag aatataaata atcacaaaat attaaataca   2520
cttaaaattt acatataaat ttacaaaaca tctaattaat tgaaacagaa aggaaaggt    2580 aaaatatatc ataaaatgag acatatatcc tataaaaaaa aaatgaggca tatgaagtaa   2640
ataataagag acatgcatgt aagcattcgg ttaattaatc gagtcaaaga tatatatcag   2700
taaatacata tgtgtatatt tctggaaaaa gaatatatat attgagaaat aagaaagat    2760 gaaa atg gaa aat ggt atg tat aaa aag aaa gga gtg tgc gac tct tgt   2809
     Met Glu Asn Gly Met Tyr Lys Lys Lys Gly Val Cys Asp Ser Cys
     1               5                   10                  15 gtc tcg tcc aaa agc aga tcc aac cac agc ccc aaa aga agc atg atg    2857
Val Ser Ser Lys Ser Arg Ser Asn His Ser Pro Lys Arg Ser Met Met
                20                  25                  30 gag cct cag cct cac cat ctc ctc atg gat tgg aac aaa gct aat gat    2905
Glu Pro Gln Pro His His Leu Leu Met Asp Trp Asn Lys Ala Asn Asp
            35                  40                  45 ctt ctc aca caa gaa cac gca gct ttt ctc aat gat cct cac cat ctc    2953
```

```
Leu Leu Thr Gln Glu His Ala Ala Phe Leu Asn Asp Pro His His Leu
        50                  55                  60 atg tta gat cca cct ccc gaa acc cta att cac ttg gac gaa gac gaa      3001
Met Leu Asp Pro Pro Pro Glu Thr Leu Ile His Leu Asp Glu Asp Glu
 65                  70                  75 gag tac gat gaa gac atg gat gcg atg aag gag atg cag tac atg atc      3049
Glu Tyr Asp Glu Asp Met Asp Ala Met Lys Glu Met Gln Tyr Met Ile
 80                  85                  90                  95 gcc gtc atg cag ccc gta gac atc gac cct gcc acg gtc cct aag ccg      3097
Ala Val Met Gln Pro Val Asp Ile Asp Pro Ala Thr Val Pro Lys Pro
                100                 105                 110 aac cgc cgt aac gta agg ata agc gac gat cct cag acg gtg gtt gct      3145
Asn Arg Arg Asn Val Arg Ile Ser Asp Asp Pro Gln Thr Val Val Ala
                115                 120                 125 cgt cgg cgt cgg gaa agg atc agc gag aag atc cga att ctc aag agg      3193
Arg Arg Arg Arg Glu Arg Ile Ser Glu Lys Ile Arg Ile Leu Lys Arg
                130                 135                 140 atc gtg cct ggt ggt gcg aag atg gac aca gct tcc atg ctc gac gaa      3241
Ile Val Pro Gly Gly Ala Lys Met Asp Thr Ala Ser Met Leu Asp Glu
145                 150                 155 gcc ata cgt tac acc aag ttc ttg aaa cgg cag gtg agg att ctt cag      3289
Ala Ile Arg Tyr Thr Lys Phe Leu Lys Arg Gln Val Arg Ile Leu Gln
160                 165                 170                 175 cct cac tct cag att gga gct cct atg gct aac ccc tct tac ctt tgt      3337
Pro His Ser Gln Ile Gly Ala Pro Met Ala Asn Pro Ser Tyr Leu Cys
                180                 185                 190 tat tac cac aac tcc caa ccc tga tgaactacac agaagctcgc tagctagaca     3391
Tyr Tyr His Asn Ser Gln Pro
                195 tttggtgtca tcctctcaac ctttttcatg ttgatatatt atatatagat gcataaagat    3451 tcgatccaag attgtatggg tgttttaata ttattattct aagatatatg atgtacaatt    3511 gtgtaccaag tttctttatc ttgatatcat atgcataaat aattggtgaa taaaagaag     3571 atattgattg taaacaaaaa aaagaagata ttgattgtta attagggttt gatcattctg    3631 tatgaaagct ttggcctgca aattaatttt cgatatatat atatatatat ggagaatata    3691 tatcaaatac ttttttaatt tgactataat ttgtatcaat tatctgaatc tgatgagtgt    3751 aggttatata tggattagca aaaagaaaa caaccattat tacgcaccta cattaaaaat     3811 catccaccaa agaagaaacc atcctcaaga gggttccctc tagag                    3856

<210> SEQ ID NO 2
<211> LENGTH: 198
<212> TYPE: PRT
<213> ORGANISM: Arabidopsis thaliana
<220> FEATURE:
<223> OTHER INFORMATION: INDEHISCENT1 (IND1) protein

<400> SEQUENCE: 2

Met Glu Asn Gly Met Tyr Lys Lys Lys Gly Val Cys Asp Ser Cys Val
  1               5                  10                  15

Ser Ser Lys Ser Arg Ser Asn His Ser Pro Lys Arg Ser Met Met Glu
                 20                  25                  30

Pro Gln Pro His His Leu Leu Met Asp Trp Asn Lys Ala Asn Asp Leu
            35                  40                  45

Leu Thr Gln Glu His Ala Ala Phe Leu Asn Asp Pro His His Leu Met
        50                  55                  60

Leu Asp Pro Pro Pro Glu Thr Leu Ile His Leu Asp Glu Asp Glu Glu
 65                  70                  75                  80
```

Tyr Asp Glu Asp Met Asp Ala Met Lys Glu Met Gln Tyr Met Ile Ala
             85                  90                  95

Val Met Gln Pro Val Asp Ile Asp Pro Ala Thr Val Pro Lys Pro Asn
            100                 105                 110

Arg Arg Asn Val Arg Ile Ser Asp Pro Gln Thr Val Val Ala Arg
            115                 120                 125

Arg Arg Arg Glu Arg Ile Ser Glu Lys Ile Arg Ile Leu Lys Arg Ile
        130                 135                 140

Val Pro Gly Gly Ala Lys Met Asp Thr Ala Ser Met Leu Asp Glu Ala
145                 150                 155                 160

Ile Arg Tyr Thr Lys Phe Leu Lys Arg Gln Val Arg Ile Leu Gln Pro
                165                 170                 175

His Ser Gln Ile Gly Ala Pro Met Ala Asn Pro Ser Tyr Leu Cys Tyr
            180                 185                 190

Tyr His Asn Ser Gln Pro
        195

<210> SEQ ID NO 3
<211> LENGTH: 2765
<212> TYPE: DNA
<213> ORGANISM: Arabidopsis thaliana
<220> FEATURE:
<223> OTHER INFORMATION: 5' untranslated region IND1 promoter

<400> SEQUENCE: 3

```
ctctagacca tctactatcc ggttgttgac ccttaaagct tttgaagact actagaataa      60
tgcaaatacc atatgtccat atccatcctt ttcttttgtt tgaactgaac attctaattt     120
tgtaaaagaa aaaaccttat gttaatatca ccgtaggcaa aaaaaatatc tcatcatatt     180
aaatttttat tataagatta tacattctct cgttgtaaga gttactccaa ttgcaagtgt     240
tgtattaact aataaaaagg acgaaagtag gaagcttata attaattgat gttgcatagt     300
actggtatat tgttgatgaa tataacaagt atgaacatta atgcatgaaa cggggtattt     360
tgtcttgaac tcattaaagg caatgtgaaa agaagatgtg aggtctcatt ttgaaaattt     420
atcttctagc tttgtcgatt ttaaatctat gaatgaacg caacatatag aaatttcatg     480
tggacaacga catttagacg gtatcttaat tagaccgatt aattagtaat atacttatat     540
atataattag tggtgattat aagtttactt atccacttga gaatttaaac aatgggcaat     600
accttaatgt cgaaagaagc cgtccccact tcgtgtaatg agttatgggg gagagatcct     660
gttaaatcgt caaataaaac aacttaagaa ctagaaattg acaccaaaaa tcataaagag     720
aacgttgaag aagtcattta tcgtatccag ctcatatttc ctagctaaga tcaaatcaag     780
gccgttgaaa gggcttgtaa gaaaatgtcg aagaaccgt ggggtttaga agaaagacaa     840
gaaatagaag aacaatgatg ttaaattgcc tattttggtg tataggagtt gtcaaaagag     900
gagagagaga agaaaattag gtcaaaataa tgagcactaa aaatggagac atgtgttgag     960
taactattac aagagcgact tatgcttcct tatggcaatg atatccaaac caaagtgcaa    1020
cgctcctttt ttgccctaat ttcgtaaagt ctctctcctt cttcgtcctt aggaaaaacc    1080
ctagaaattt aatcccttgt tcttgatctt gcttttgag taaccatgat tttgaccaca    1140
cactatttct tctatctttt gtggtctata ggattttgct ttatatgtgt ttcttgtatt    1200
gctccgtacg tacgtatacg aatttaaatg gttataacaa ggtttatata aactagcaca    1260
aatgagtcca tgaaatttgt tagcgaaaaa ggtagaaata tattgagtct ttaaacggca    1320
```

```
atatatataa ttttgctgca aaacttagct ttaatcatga tctaatgata ttttctttaa    1380
tttcctttgc caaattaatc acatgcacgg attttttggca agttatgtgt cgaattcttc   1440
cattcacaca acactaaact taattagaac tctaggaaat attttaaaat gacaacttta   1500
tcgaaaaaaa tttagttatg aaacaattc cagaattaaa catgagctat ataatttaag    1560
ataaaatgaa gtaatattga tatgtatgta ataacatatc tgattgcggt aaaaaaaaac   1620
atatctgatt aaattgttca tgcaggccca tgtcactatg atgtcatcac gttttattt    1680 tcacaataac taatatatat tcaaaaaaat agttttgtca gattaaattt ttttggtgg    1740 tcagctttct ccaacctact aaactagttt ggaatgttct cttctttatt tttctttttc   1800
ttgatttctt atgttttta tttatggaat tttaagacgg attgtttagg tcgtttctct    1860
cttttcttgt tttctaaagt tacttttgta aactcatctc ctcccaatta gacagtcaat   1920
catatagtta tcttttaata tatgtctagt tgataaaaaa aatgaaaaaa tactggtggt   1980
agttctacta atgtttgtgt aaaaaatctg atattatgaa tctaatcaat ttctttgatc   2040
gtataatgtg ggttaaattt agtaattttt tacataaata agaactgtaa tgttgatgta   2100
tattggggaa tcagtatatt agcttgggta actatacttc tggaaatact tgaagattta   2160
actatttgca aaattataat ttagtcccga aaaatacaga cgacgggaca cgacaacata   2220
taagcaggtt tgaatcttgg aaaattttgt atacataacc tatataaata ctaatgttct   2280
ggttgggttc aaaagccttt tcaaaagttc catttttaa attcaaggac attttacata    2340
ggaaataagt tgagtcataa aaaataatgg ttattttgta aggttttttt tttgattaaa   2400
acgcacatat taagaagtta gttttttttc actaccaaat atcaattaat ttaaaccat    2460 gcaaccattc ataaaacaat actattaaag aatataaata atcacaaaat attaaataca   2520
cttaaaattt acatataaat ttacaaaaca tctaattaat tgaaacagaa aggaaaaggt   2580
aaaatatatc ataaaatgag acatatatcc tataaaaaaa aaatgaggca tatgaagtaa   2640
ataataagag acatgcatgt aagcattcgg ttaattaatc gagtcaaaga tatatatcag   2700
taaatacata tgtgtatatt tctggaaaaa gaatatatat attgagaaat aagaaaagat   2760
gaaaa                                                               2765
```

<210> SEQ ID NO 4
<211> LENGTH: 496
<212> TYPE: DNA
<213> ORGANISM: Arabidopsis thaliana
<220> FEATURE:
<223> OTHER INFORMATION: 3' untranslated region IND1 promoter

<400> SEQUENCE: 4

```
atgaactaca cagaagctcg ctagctagac atttggtgtc atcctctcaa cctttttcat     60
gttgatatat tatatataga tgcataaaga ttcgatccaa gattgtatgg gtgttttaat   120
attattattc taagatatat gatgtacaat tgtgtaccaa gtttctttat cttgatatca   180
tatgcataaa taattggtga ataaaaagaa gatattgatt gtaaacaaaa aaagaagat    240 attgattgtt aattagggtt tgatcattct gtatgaaagc tttggcctgc aaattaattt   300
tcgatatata tatatatata tggagaatat atatcaaata ctttttttaat ttgactataa   360 tttgtatcaa ttatctgaat ctgatgagtg taggttatat atggattagc aaaaaagaaa   420
acaaccatta ttacgcacct acattaaaaa tcatccacca agaagaaac catcctcaag    480 agggttccct ctagag                                                   496
```

```
<210> SEQ ID NO 5
<211> LENGTH: 5622
<212> TYPE: DNA
<213> ORGANISM: Arabidopsis thaliana
<220> FEATURE:
<223> OTHER INFORMATION: SHATTERPROOF1 (SHP1) genomic
<221> NAME/KEY: modified_base
<222> LOCATION: (935)..(941)
<223> OTHER INFORMATION: n = any nucleotide

<400> SEQUENCE: 5
```

| | | | | | |
|---|---|---|---|---|---|
| agatctgcaa | cagtgaaaag | agaaaacaaa | atggacttga | agaggttttg | acaatgccag | 60 |
| agataatgct | tattccctaa | tatgttgcca | gccaagtgtc | aaattggctt | tttaaatatg | 120 |
| gatttctgta | tcagtggtca | tatttgtgga | tccaacgtat | tcatcatcaa | gttctcaagt | 180 |
| ttgctttcag | tgcaattcta | attcacacgt | ttaactttaa | catgcatgtc | attataatta | 240 |
| cttcttcact | aagacacaat | acggcaaacc | tttcagatta | tattaatctc | cataaatgaa | 300 |
| ataattaacc | tcataatcaa | gattcaatgt | ttctaaatat | atatggacaa | aatttacacg | 360 |
| gaagattaga | tacgtatatt | agtagattta | gtctttcgtt | tgtgcgataa | gattaaccac | 420 |
| ctcatagata | gtaatatcat | tgtcaaattc | ctctcggttt | agtcgctaaa | ttgtatcttt | 480 |
| tttaagccta | aaagtagtgt | attcgcatat | gacttatcgt | cctaactttt | tttttaatta | 540 |
| acaaaaaaat | cgaaagaaa | ataatctgtt | aaatattttt | taagtactcc | attaagttta | 600 |
| gtttctattt | aaaaaatgct | tgaaatttga | cagttatgtt | caacaatttt | gaatcatgag | 660 |
| cgatgtctag | atactcagaa | tttaatcaag | atgtcttatc | aaatttgttg | tcactcgagg | 720 |
| acccacgcaa | agaaaagac | taatatgatt | tttatttggt | ctggatattt | tgtagagga | 780 |
| tgaaactaag | agagtgaaag | attcgaaatc | cacaatgttc | aagagagctc | aaagcaaaaa | 840 |
| gaaaatgaa | gatgaaggac | taagaacaa | taagcaacta | cttatacccct | atttccataa | 900 |
| aggattcagg | tactaggaga | agttgaggca | agttnnnnnn | nattgattca | aattttcatt | 960 |
| tattttaca | atttaattca | cctaagttat | tatgcatttc | tcatcattgg | tacatttct | 1020 |
| gtatagcgta | tttacatata | tgaaataaat | taaatatgtc | ctcacgttgc | aagtagttaa | 1080 |
| tgaatgtccc | cacgcaaaaa | aaatccctc | caaatatgtc | cacctttct | tttcttttta | 1140 |
| attccaaaat | taccataaac | ttttggttta | caaagattt | ctagaaattg | aggaagatat | 1200 |
| cctaaatgat | tcatgaatcc | ttcaataatc | tgaagtttgc | gatattttcg | attttcttca | 1260 |
| agagttgcga | tatttgtaat | ttggtgacct | taaacttttt | ttgataaaga | gtaaacgttt | 1320 |
| tttcttaaaa | gtaaaacttg | attttatgtt | ttagggttct | agctcaactt | tgtattatat | 1380 |
| ttcttgcaaa | aagagttcgt | taactgcatt | cttcaacact | ataaagtgat | tatcaaaaac | 1440 |
| atcttcatga | acattaagaa | aaacaatatt | tggtttcggt | tagagcttgg | ttttgcttgg | 1500 |
| cttgattcac | atacccattc | tagactttgg | cataaatttg | atacgataga | gagtatctaa | 1560 |
| tggtaatgca | gaagggtaaa | aaaaggaaga | gagaaaaggt | gagaaagatt | accaaaaata | 1620 |
| aggagtttca | aagatggtt | ctgatgagaa | acagagccca | tccctctcct | tttccccttc | 1680 |
| ccatgaaaga | aatcggatgg | tcctccttca | atgtcctcca | cctactcttc | tcttctttct | 1740 |
| tttttcttt | cttattatta | accatttaat | taatttcccc | ttcaatttca | gtttctagtt | 1800 |
| ctgtaaaaag | aaaatacaca | tctcacttat | agatatccat | atctatttat | atgcatgtat | 1860 |
| agagaataaa | aaagtgtgag | tttctaggta | tgttgagtat | gtgctgtttg | gacaattgtt | 1920 |
| agatgatctg | tccatttttt | tcttttttct | tctgtgtata | aatatatttg | agcacaaaga | 1980 |
| aaaactaata | accttctgtt | ttcagcaact | agggtcttat | aaccttcaaa | gaaatattcc | 2040 |

```
ttcaattgaa aacccataaa ccaaaataga tattacaaaa ggaaagagag atatttcaa    2100
gaacaacata attagaaaag cagaagcagc agttaagtgg tactgagata aatgatatag   2160
tttctcttca agaacagttt ctcattaccc accttctcct ttttgctgat ctatcgtaat   2220
cttgagaact caggtaaggt tgtgaatatt atgcaccatt cattaaccct aaaaataaga   2280
gatttaaaat aaatgtttct tctttctctg attcttgtgt aaccaattca tgggtttgat   2340
atgtttcttg gttattgctt atcaacaaag agatttgatc attataaagt agattaataa   2400
ctcttaaaca cacaaagttt ctttatttt tagttacatc cctaattcta gaccagaaca    2460
tggatttgat ctatttcttg gttatgtatc ttgatcagga aaagggattt gatcatcaag   2520
attagccttc tctctctctc tctagatatc tttcttgaat ttagaaatct ttatttaatt   2580
atttggtgat gtcatatatg gatcaatgga ggaaggtggg agtagtcacg acgcagagag   2640
tagcaagaaa ctagggagag ggaaaataga gataaagagg atagaaaca caacaaatcg    2700
tcaagttact ttctgcaaac gacgcaatgg tcttctcaag aaagcttatg aactctctgt   2760
cttgtgtgat gccgaagttg ccctcgtcat cttctccact cgtggccgtc tctatgagta   2820
cgccaacaac aggtacgctt ctcctactct atttcttgat cttgttttct taattttaac   2880
taaacaagat cctagttcaa atgataacaa agtggggatt gagagccaag attagggttt   2940
ggttaattta gaaaaccaga tttcacttgt tgatacattt aatatctctc tagctagatt   3000
tagtactctc tcctctatat atgtgtgggt gtgtgtgtaa gtgtgtatat gtatgcaaat   3060
gcaagaagaa gaagaaaaag ttatcttgtc ttctcaaatt ctgatcagct ttgaccttag   3120
tttcactctt ttttctgcaa atcatttgaa cctgatgcat gtcagtttct acaatacact   3180
tttaattttg acggcccatc aaatttccta gggtttactt cagtgaacaa aattgggttc   3240
ttgacacgat ttagcatgta tatataaaaa tagggggatga tcaagactta tgtaacctct   3300
gtctggtgaa actagggaca aagtctactg atgagttgtc actagggatc catttgatca   3360
tttaatccca acaaaaatga aacaaaattt tgagaattta tatgctgaag ttttccaacc   3420
ctcttttta aataacttta tattatgtag atttgtattt agggtaattt gtccaactag    3480
aagtcctaaa aatcaataaa cacacggatg actttgtcta acattgtatc agtcatcaaa   3540
tgtaaaattg tacaaataat gaaattaaag atttagtctc tttttatttt tttgtttagg   3600
gtgtatatat atatatatat gtatatttgt tgcattgata tatcaatgag agggagagaa   3660
ctcagagaag tgtcggaaat taaatggta cgagccaatt ggaatctctg cattctgag     3720
cttcatttgt ttgttattag aaaaaaaaa aaaaatcct ttaaagatac cttcatgatg     3780
acattgaatc atgtaatata cacgatacat ggtctaattc ctcctcaaac cctaattacc   3840
aatttcgaaa ccataatatt tactagtatg tttatatatc cttactttaa gacattgttt   3900
gtttataata ccttgtgaat taagaaaaaa aaaaaaaac ttgtggatct attcaagcca    3960
tgtgttagaa taaatttata aattttctcc tcgtactggt cagatattgg tccaaactcc   4020
aaagccttcc cttttcagga aaaaaaacat ttcgaaatta actctaatta atcaagaatt   4080
tcctacaatg tatacatcta atgttttttc cgcgatctta cttattagtg tgagggtac    4140
aattgaaagg tacaagaaag cttgttccga tgccgtcaac cctccttccg tcaccgaagc   4200
taatactcag gtaccaattt atattgtttg attctctttg ttttatcttc ttcttttcat   4260
tatatatatg atcaacaaaa aatataacct acaaaagag agagttcaag gaaatgcatt    4320
gaaacggttt cgttatggtg tttgaataca tggattttg aagtactatc agcaagaagc    4380
```

-continued

```
ctctaagctt cggaggcaga ttcgagatat tcagaattca aataggtaat tcattaactt      4440
ttcatgaact cttcgatttg gtattaggtc acttaatttg gtgtcggtcc aaaagtccgc      4500
ttgtagtttt ctttagaagt tgttttgttt aatgttcatg tttacaaatt gaaggcatat      4560 tgttgggggaa tcacttggtt ccttgaactt caaggaactc aaaaacctag aaggacgtct     4620
tgaaaaagga atcagccgtg tccgctccaa aaagtaaaaa tctacgttgc tctctctctg     4680
tgtctctgtc tctctctcta tatatagtcc cttagtttat atagttcatc accctttgt      4740 gagaattttg cagaatgagc tgttagtggc agagatagag tatatgcaga agagggtaag      4800
aacgtttctc ccattccaag taattagatc tttcttcgtc tttgtgaggg tttgagtttt      4860
cccataaatc atgtgtagga aatggagttg caacacaata acatgtacct gcgagcaaag      4920
gttagccacg ttctgttcca aatcttaatc tcaatatcta ctcttttctt cattgtataa      4980
ctaagataac gtgaataaca agaaaacttt tgttttgggg tttaatagat agccgaaggc      5040
gccagattga atccggacca gcaggaatcg agtgtgatac aagggacgac agtttacgaa      5100
tccggtgtat cttctcatga ccagtcgcag cattataatc ggaactatat tccggtgaac      5160
cttcttgaac cgaatcagca attctccggc caagaccaac ctcctcttca acttgtgtaa      5220
ctcaaaacat gataacttgt ttcttcccct cataacgatt aagagagaga cgagagagtt      5280
catttttatt ttataacgcg actgtgtatt catagtttag gttctaataa tgataataac      5340
aaaactgttg tttctttgct taattacatc aacatttaaa tccaaagttc taaaacacgt      5400
cgagatccaa agtttgtcat acaagattag acgcatacac gatcagttaa tagattttaa      5460
gtgcctttta atatttacat atagttgcag cttcgattag atcatgtcca ccaaacactc      5520
acaattagag acaagcaaaa ctataaacat tgatcataaa atgattacaa catgtccata      5580
aattaattat ggattacaaa aataaaaact tacaaaagat ct                         5622
```

<210> SEQ ID NO 6
<211> LENGTH: 6138
<212> TYPE: DNA
<213> ORGANISM: Arabidopsis thaliana
<220> FEATURE:
<223> OTHER INFORMATION: SHATTERPROOF2 (SHP2) genomic

<400> SEQUENCE: 6

```
gaattcgtaa cagaatttag tgaataatat tgtaattacc aggcaaggac tctccaaacg       60
gatagctcga atatcgttat taaagagtaa atgatccaat atgtaagcca ttgttgatca      120
tctaacattg ttggactctc tattgctcga aatgatgcat acctaatcat ttattcagtt      180
aactatcaag ttgcatttgt aaaaaccaaa catttaaatt cagatttgat atcacttaca      240
gaggatagag aagcatgact ccaggcctgc atgcaacaag aaaaaggaag aaaataatgt      300 taaaatttg acaaatatag tgtttatttt tattatatga gacagaattt gaataaaatc      360
ctacccaact agagcatcaa aacgttttgc aatcgcaata atgaaaccca tttctttttt     420 gagttttttac tcttctttca acagaaactt tctcaaacgt ctttagcact gtgacgttag     480
atatatacac aaaagcttga aatttcttca agcaaaagaa tctttgtggg agttaaggca     540
acaagccagg taagaatct ccaacgcatt gttacgtttt catgaaccta tttattatat       600
gttctaagaa agaaaaaaat atctcaaagt aaacgttgga aattttctga tgaagggaaa     660
tccaaagtct tgggtttagt atccctatga atggtatttg aatatgtttt cgtcaaaac      720 aaaagattcc tttctttttc acaagagtta gtgatcaata acttatgcac taattaatga     780
gattggacgt atacacaatt tgattatgat acttgagtaa aaatcacctg tccttttaatt    840
```

-continued

```
tggaaatctc tctttcttac ccatttatat actacttctt ttcattaaaa ttaaatttca      900
attatcaatc atcgttcaat ttgataaaga tttaacattt tttgtcacag ggctagtaaa      960
agcaatcttt acataattca tctttcttac atatatatat taccttttc ttcattagta     1020
ttctatttga ttatgattat tttgtcataa agctagtaaa ttaaacactc gatatgagaa     1080
ttatattact tcacgctaat taactcttaa cacaacaaga actagtgcat attcaacttt     1140
caaagcatat actatatatt gagaatatag accacgaaag tcaatcaaaa gacctaccag     1200
ctctcatcaa gttctttctt gaaatgattt tgcagaattt ccaacttaat taattcgaca     1260
tgaatgtgaa aatgtgtgtt gctcgttaag aaaattgaat agaagtacaa tgaaaatgat     1320
gaggaatggg caaacacaa aagagtttcc tttcgtaact acaattaatt aatgcaaatc      1380
tgagaaaggg ttcatggata atgactacac acatgattag tcattccccg tgggctctct     1440
gctttcattt actttattag tttcatcttc tctaattata ttgtcgcata tatgatgcag     1500
ttcttttgtc taaattacgt aatatgatgt aattaattat caaataaat attcaaattg      1560
ccgttggact aacctaatgt ccaagattaa gacttgaaca taagaatttt ggaaaaacta    1620
aaccagttat aatatatact cttaaattgc catttctgaa cacaaccaaa taataatata    1680
tactatttac agttttttt aattggcaag aacactgaaa tcttattcat tgtctcgctt     1740
ggtagttgac aagttataac actcatattc atataaccc attctaacgt tgacgacgaa     1800
cactcatata aaccaccaa attcttagca tattagctaa atattggttt aattggaaat     1860
atttttttta tatataaaat gccaggtaaa tattaacgac atgcaatgta tataggagta    1920
gggcaataaa aagaaaagga gaataaaaag ggattaccaa aaaaggaaag tttccaaaag    1980
gtgattctga tgagaaacag agcccatacc tctcttttt cctctaaaca tgaaagaaaa     2040
attggatggt cctccttcaa tgctctctcc ccacccaatc caaacccaac tgtcttcttt    2100
cttcttttt tcttctttct aatttgatat tttctaccac ttaattccaa tcaatttcaa    2160
atttcaatct aaatgtatgc atatagaatt taattaaaag aattaggtgt gtgatatttg    2220
agaaaatgtt agaagtaatg gtccatgttc tttctttctt tttccttcta taacacttca    2280
gtttgaaaaa aaactaccaa accttctgtt ttctgcaaat gggtttttaa atacttccaa    2340
agaaatattc tctaaaaga aattataaac caaacagaa accaaaaaca aaaataaag      2400
ttgaagcagc agttaagtgg tactgagata ataagaatag tatctttagg ccaatgaaca    2460
aattaactct ctcataattc atcttcccat cctcacttct ctttctttct gatataatta    2520
atcttgctaa gccaggtatg gttattgatg atttacactt tttttaaaa gtttcttcct     2580
tttctccaat caaattcttc agttaatcct tataaaccat ttctttaatc caaggtgttt    2640
gagtgcaaaa ggatttgatc tatttctctt gtgtttatac ttcagctagg cttatagaa    2700
atggagggtg gtgcgagtaa tgaagtagca gagagcagca agaagatagg gagagggaag    2760
atagagataa agaggataga gaacactacg aatcgtcaag tcactttctg caaacgacgc    2820
aatggtttac tcaagaaagc ttatgagctc tctgtcttgt gtgacgctga ggttgctctt    2880
gtcatcttct ccactcgagg ccgtctctac gagtacgcca acaacaggta cacatcttt    2940
agctagatct tgattttgtt gaattttttt tctagaataa agtttcgact cttctggtgg    3000
gttttttcaat ctttatggtc tctttatagt ttttttcctt agtttctctg aagctcaaat  3060
ctctttaaaa atccccaaaa ttagggtttg tttaaaacta gggaacccta ctttaacttc    3120
tttctcttag taaaaaagca gtgagggtct tctctgatca ttaattagca tcccccatac    3180
```

```
cttgttccag tcacttttc tccacaaatc cttataacag tatctatata tgtatctatt    3240
tatgtcagtt tgtacaagac acttcgatca atttgatgac ccatcaagtt ttatttctgc    3300
agattgatca ttaggtttcc atcatagtaa tgaaaaagta gggttcttga taaaattata    3360
ataatatata ttatttggct atataaaaaa gctatgtaga ttccttaaaa attgattcac    3420
tagggagaga ctagtaggtg tttgtcttct gacacttctc taatcttttg gtgaatcctt    3480
ttgttaaatc aagaaaatga atcagggaca aagcttattg ttgagtcact taattaatca    3540
tccgatccat caatcaagaa aaataacgaa acagaaaatt ttgattttg attgttattt    3600
tctccacttc aagttgggga cttgtcattt ccgttttct atacgtttcc agctattaac    3660
agctcatgtt catttcacca ttttgattat ttgtctgctt tttaaagata aatgttttca    3720
aaaatattgt ttttatttgc ttggctagtt aatactataa ttgaggttga tgtatgacta    3780
taatctataa gtcaagtctc atatcatgga tctaagttaa aactagtaaa tttgtagttt    3840
caatgtgaac tttcacaacg actaaagaac tgatctgaag tttataatgg acatgactaa    3900
tttgattaac aaaagaggaa tgcattatgt atgtagaaac atgtgatata tatatgtttc    3960
tattatcaaa agtgtagtta actttcttat ttcaaacacc ctcatgcttt agtagtatct    4020
tacttttgac atttctcaac ttcagctttc cattatacaa cagcacaatg taaattactt    4080
gtatatgaat atgaaagcat aacgttatgc aaagatttct agcttttctt tttctgtttt    4140
gcaaaagatt tacaaatatc atgttcttgg taaaaacata cttgcctcag ccacatatgc    4200
atgtaaatgt aatgttcaaa tattaattca ggaaaaacaa agaagaagca aaattagctt    4260
ctagagtagg gaatctattg acttgacctg aaaatcactt ctttttctta aagcctagta    4320
gtgaattttt taatctaatt aggccaaaat atatactagc ctaaaatata atttggatttt    4380
tgtgtcgtac ataaattggg accaattcca attaactaag agcatatgca attcaaattc    4440
ttttttatttt cttctccgat ttgctacttc tttctttgt atgttttcaa attaggatta    4500
cactttttg gggaagtaca cattagggtc ttctcgaact ttgattatac atatatatat    4560
atatatatat ataactttt gtgagatgtc actgttaata gataataggc aataacaata    4620
atatccaaaa aagaaggcgc aaacaaatca tatactatat ggtactggtc cattcactat    4680
tttgtcggtt gaatttaagg tttggcgtac aaactttgtt tcaaaccttt attattccgt    4740
cttttctgtgt gttttgtata tccagaagat aaaaatatca atttctttaa cgacttcata    4800
tatatatata tatatatata tatatatatt tttctcttct ggttttagtg tttgaatcca    4860
acagttatag tttcgtgtgt ctttgtttta cttgtggtgg tttaagtttg agattttcac    4920
cgattgcatc tatttacata tatagctacc acaaaaaaga ttgcatttta aaatcttttc    4980
ctttgtgtga atgttgatga agtgtgagag gaacaataga aaggtacaag aaagcttgct    5040
ccgacgccgt taaccctccg accatcaccg aagctaatac tcaggttagc ttttaattaa    5100
tacacctagc tagctagttc gttaattact taatttcttc ttcttttagt tatctgacct    5160
tttttcacc tcttgtaaca atgatgggat cgaaattgat gaagtactat cagcaagagg    5220
cgtctaaact ccggagacag attcgggaca ttcagaattt gaacagacac attcttggtg    5280
aatctcttgg ttccttgaac tttaaggaac tcaagaacct tgaaagtagg cttgagaaag    5340
gaatcagtcg tgtccgatcc aagaaggtac atcactaact ctccatcaat ctccttatca    5400
ttgaatatat atccatctga ttcttgcccg ttatatttgg ttttctctc cagcacgaga    5460
tgttagttgc agagattgaa tacatgcaaa aaagggtaaa agtaaaacct atcttccttc    5520
acaatgaact accctactt tattagcaac ttctctttct gatgatcatc ttttttattt    5580
```

-continued

```
tctgttgtcg cttgcattgt aggaaatcga gctgcaaaac gataacatgt atctccgctc    5640
caaggtttta tacataactc tttttggcat ttttgatcat catttttttc cggtagacaa    5700
tctcttgatg tgcaaattct aaatatctct gcagattact gaaagaacag gtctacagca    5760
acaagaatcg agtgtgatac atcaagggac agtttacgag tcgggtgtta cttcttctca    5820
ccagtcgggg cagtataacc ggaattatat tgcggttaac cttcttgaac cgaatcagaa    5880
ttcctccaac caagaccaac cacctctgca acttgtttga ttcagtctaa cataagcttc    5940
tttcctcagc ctgagatcga tctatagtgt cacctaaatg cggccgcgtc cctcaacatc    6000
tagtcgcaag ctgaggggaa ccactagtgt catacgaacc tccaagagac ggttacacaa    6060
acgggtacat tgttgatgtc atgtatgaca atcgcccaag taagtatcca gctgtgttca    6120
gaacgtacgt ccgaattc                                                  6138
```

```
<210> SEQ ID NO 7
<211> LENGTH: 51
<212> TYPE: PRT
<213> ORGANISM: Artificial Sequence
<220> FEATURE:
<223> OTHER INFORMATION: Description of Artificial Sequence:IND1 basic
      helix-loop-helix (bHLH) DNA binding domain

<400> SEQUENCE: 7

Ile Ser Asp Asp Pro Gln Thr Val Val Ala Arg Arg Arg Glu Arg
  1               5                  10                  15

Ile Ser Glu Lys Ile Arg Ile Leu Lys Arg Ile Val Pro Gly Gly Ala
             20                  25                  30

Lys Met Asp Thr Ala Ser Met Leu Asp Glu Ala Ile Arg Tyr Thr Lys
         35                  40                  45

Phe Leu Lys
     50
```

```
<210> SEQ ID NO 8
<211> LENGTH: 26
<212> TYPE: DNA
<213> ORGANISM: Artificial Sequence
<220> FEATURE:
<223> OTHER INFORMATION: Description of Artificial Sequence:primer for
      amplification of IND1 genomic region of cDNA

<400> SEQUENCE: 8
gatgaaaatg gaaaatggta tgtata                                          26
```

```
<210> SEQ ID NO 9
<211> LENGTH: 23
<212> TYPE: DNA
<213> ORGANISM: Artificial Sequence
<220> FEATURE:
<223> OTHER INFORMATION: Description of Artificial Sequence:primer for
      amplification of IND1 genomic region of cDNA

<400> SEQUENCE: 9
gttcatcagg gttgggagtt gtg                                             23
```